United States Patent
Adams et al.

(10) Patent No.: US 10,247,725 B2
(45) Date of Patent: Apr. 2, 2019

(54) CAPTURE, IDENTIFICATION AND USE OF A NEW BIOMARKER OF SOLID TUMORS IN BODY FLUIDS

(71) Applicant: CREATV MICROTECH, INC., Potomac, MD (US)

(72) Inventors: Daniel Adams, Kensington, MD (US); Cha-Mei Tang, Potomac, MD (US)

(73) Assignee: CREATV MICROTECH INC., Potomac, MD (US)

( * ) Notice: Subject to any disclaimer, the term of this patent is extended or adjusted under 35 U.S.C. 154(b) by 0 days.

(21) Appl. No.: 14/404,403

(22) PCT Filed: May 31, 2013

(86) PCT No.: PCT/US2013/043610
§ 371 (c)(1),
(2) Date: Nov. 26, 2014

(87) PCT Pub. No.: WO2013/181532
PCT Pub. Date: Dec. 5, 2013

(65) Prior Publication Data
US 2015/0168381 A1  Jun. 18, 2015

Related U.S. Application Data

(60) Provisional application No. 61/654,636, filed on Jun. 1, 2012, provisional application No. 61/773,026, filed on Mar. 5, 2013, provisional application No. 61/787,863, filed on Mar. 15, 2013.

(51) Int. Cl.
G01N 33/50 (2006.01)
G01N 33/574 (2006.01)

(52) U.S. Cl.
CPC ... *G01N 33/5091* (2013.01); *G01N 33/57488* (2013.01); *G01N 2800/52* (2013.01)

(58) Field of Classification Search
CPC .............................................. G01N 33/57488
See application file for complete search history.

(56) References Cited

U.S. PATENT DOCUMENTS 7,993,826 B2   8/2011  Giesing et al.
8,551,425 B2 * 10/2013  Goldkorn ............. C12N 5/0693
                                                      210/650
2006/0178833 A1   8/2006  Bauer et al.
2014/0315295 A1  10/2014  Makarova et al.

FOREIGN PATENT DOCUMENTS

| WO | 2007/089911 | 8/2007 |
| WO | 2009/092068 | 7/2009 |
| WO | 2010/028160 | 3/2010 |
| WO | 2010/047682 | 4/2010 |
| WO | 2010/111388 | 9/2010 |
| WO | 2011/002649 A1 | 1/2011 |
| WO | 2011/139445 A1 | 11/2011 |
| WO | 2013/181532 | 12/2013 |

OTHER PUBLICATIONS

Amani et al. IJI, 2005, 2(2):117-122.*
International Search Report and Written Opinion for PCT/US2013/043610, dated Nov. 1, 2013.
Faber et al. Activated macrophages containing tumor marker in colon carcinoma: immunohistochemical proof of a concept. Tumor Biol. ePub Dec. 2, 2011, vol. 33, No. 2, pp. 435-441.
Krombach et al. Cell Size of Alveolar Macrophages: An Interspecies Comparison. Environmental Health Perspectives Sep. 1997, vol. 105, Supplement 5, pp. 1261-1263.
Schmid et al. Myeloid cell trafficking and tumor angiogenesis. Cancer Lett 2007. 250(1):1-8.
Leers et al., "A Three-Color/Five-Parameter Flow Cytometric Study on Peripheral Blood Samples", Am J Clin Pathol, 129: 649-656 (2008).
Caillou et al., "Tumor-Associated Macrophages (TAMs) Form an Interconnected Cellular Supportive Network in Anaplastic Thyroid Carcinoma", PLoS ONE, 6(7): e22567 (2011).
Wang et al., "Identification and Characterization of Circulating Prostate Carcinoma Cells", Cancer, 88(12): 2787-2795 (2000).
Zhang et al., "Alternatively Activated RAW264.7 Macrophages Enhance Tumor Lymphangiogenesis in Mouse Lung Adenocarcinoma", Journal of Cellular Biochemistry, 107: 134-143 (2009).
Duluc et al., "Tumor-associated leukemia inhibitory factor and IL-6 skew monocyte differentiation into tumor-associated macrophage-like cells", Blood, 110(13): 4319-4330 (2007).
Morgan et al., "Molecular Profiling of Giant Cell Tumor of Bone and Osteoclastic Localization of Ligand for Receptor Activator of Nuclear Factor κb", American Journal of Pathology, 167(1): 117-128 (2005).
Extended European Search Report dated Mar. 8, 2016, issued in corresponding European Application No. 13797578.5.
Adams et al., Circulating Giant Macrophages as a Potential Biomarker of Solid Tumors, PNAS, 2014, vol. 111, No. 9, pp. 3514-3519.
Extended European Search Report dated Jan. 30, 2018 in European Application No. 15836011.5.
Extended European Search Report dated Sep. 17, 2018 in European Application No. 18179948.7.
Zhang et al., "Early Lung Cancer Diagnosis by Bioserisors", Int. J. Mol. Sci., 14: 15479-15509 (2013).
International Search Report and Written Opinion of the International Searching Authority, dated Jan. 19, 2016 in international application No. PCT/US15/46782.

* cited by examiner

*Primary Examiner* — Bin Shen
(74) *Attorney, Agent, or Firm* — Wenderoth, Lind & Ponack, L.L.P.

(57) ABSTRACT

A new sensitive cell biomarker of solid tumors is identified in blood. This biomarker can be used to determine presence of carcinomas, rapid determination of treatment response, early detection of cancer, early detection of cancer recurrence, and may be used to determine therapy.

17 Claims, 28 Drawing Sheets

(A)

(B)

(C)

(D)

(E)

(F)

(G)

(H)

(I)

CAPTURE, IDENTIFICATION AND USE OF A NEW BIOMARKER OF SOLID TUMORS IN BODY FLUIDS

BACKGROUND

Field of the Invention

The present invention relates generally to identification of a biomarker in blood and other body fluids that can be used for detection of solid tumors and to monitor efficacy of chemotherapy and radiation therapy treatments. The present invention also relates to the use of the biomarker in combination with circulating tumor cells, free plasma and serum DNA cancer markers, cancer-associated protein markers and other biomarkers.

Related Art

When tumor cells break away from primary solid tumors, they penetrate into the blood or lymphatic circulation, and ultimately leave the blood stream and enter other organ or tissue to form metastasis. 90% of cancer-related deaths are caused by the metastatic process. The most common metastatic sites are the lung, liver, bone and brain. Tumor cells found in the circulation are called circulating tumor cells (CTCs). Many research publications and clinical trials show that CTCs have clinical utility (i) by providing prognostic survival and cancer recurrence information by counting the number of cells in the blood stream, and (ii) by providing treatment information by looking at protein expressions, gene mutations and translocations in the CTCs. However, CTCs cannot be found consistently, even in stage IV patients.

Some medical conditions may be diagnosed by detecting the presence of certain types of cells in bodily fluid. In particular, cells indicative or characteristic of certain medical conditions may be larger and/or less flexible than other cells found in certain bodily fluids. Accordingly, by collecting such larger and/or less flexible cells from a liquid sample of a bodily fluid, it may be possible to diagnose a medical condition based on the cells collected.

SUMMARY

The present invention is directed to and discloses a type of cell with special characteristics that is found in the blood of cancer patients. The cell type, termed "circulating Cancer Associated Macrophage-Like cell" (CAML), is described herein and shown to be associated with the presence of solid tumors in a patient. This cell type is shown by data presented herein to have clinical utility in that it can be used as a biomarker for a variety of medical applications. This cell type has been found consistently in the peripheral blood of stage I to stage IV cancer of epithelial origin by microfiltration using precision microfilters.

CAMLs can be used as a biomarker to provide a diagnosis of cancer, in particular, an early detection of cancer, an early detection of cancer recurrence, and a determination of cancer mutation. CAMLs can also be used as a biomarker in determining appropriate courses of therapy, in particular, the cells can be used in a rapid determination of effectiveness of chemotherapy and radiation therapy treatment response.

CAMLS may be used independently as a cancer marker, and CAMLS can be used together with CTCs, free DNAs, proteins and other biomarkers in body fluids to provide a more complete understanding of the patient's disease.

More specifically, and in a first embodiment, the present invention is directed to methods of screening a subject for cancer, comprising detecting circulating cancer associated macrophage-like cells (CAMLs) in a biological sample from a subject. In particular aspects, when CAMLs are detected in the biological sample, the subject is identified as potentially having a carcinoma or solid tumor. In other aspects, when CAMLs are detected in the biological sample, the subject is identified as having a carcinoma or solid tumor. In certain aspects, the methods encompassed by this embodiment also include detecting circulating tumor cells (CTCs) in the biological sample. In particular aspects of this first embodiment, the subject is a subject suspected of having cancer.

In a second embodiment, the present invention is directed to methods for diagnosing cancer in a subject, comprising detecting CAMLs in a biological sample from a subject, wherein when CAMLs are detected in the biological sample, the subject is diagnosed with cancer. In certain aspects, the methods encompassed by this embodiment also include detecting CTCs in the biological sample, wherein when CAMLs and CTCs are detected in the biological sample, the subject is diagnosed with cancer.

In a third embodiment, the present invention is directed to methods for detecting recurrence of cancer in a subject, comprising detecting CAMLs in a biological sample from a subject previously treated for cancer, wherein when CAMLs are detected in the biological sample, recurrence of cancer is detected. In certain aspects, the methods encompassed by this embodiment also include detecting CTCs in the biological sample, wherein when CAMLs and CTCs are detected in the biological sample, recurrence of cancer is detected.

In a fourth embodiment, the present invention is directed to methods for confirming a diagnosis of cancer in a subject, comprising detecting CAMLs in a biological sample from a subject diagnosed with cancer, wherein when CAMLs are detected in the biological sample, a diagnosis of cancer is confirmed in the subject. In certain aspects, the methods encompassed by this embodiment also include detecting CTCs in the biological sample, wherein when CAMLs and CTCs are detected in the biological sample, a diagnosis of cancer is confirmed in the subject. In particular aspects, the initial cancer diagnosis is via mammography, PSA test, or presence of CA125. In a particular aspect, the subject is suspected of having cancer.

In aspects of the first through fourth embodiments, CAMLs are detected using one or more means selected from the group consisting of size exclusion methodology, red blood cell lysis, FICOLL, a microfluidic chip, and flow cytometry, or a combination thereof. In particular aspects, the size exclusion methodology comprises use of a microfilter. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution.

In certain aspects of the first through fourth embodiments, CAMLs and CTCs are simultaneously detected using a microfilter. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution.

In certain aspects of the first through fourth embodiments, CAMLs are detected using a microfluidic chip based on physical size-based sorting, hydrodynamic size-based sorting, grouping, trapping, immunocapture, concentrating large cells, or eliminating small cells based on size.

In certain aspects of the first through fourth embodiments, CAMLs are detected using a CellSieve™ low-pressure microfiltration assay.

In aspects of the first through fourth embodiments, the biological sample is one or more selected from the group consisting of peripheral blood, blood, lymph nodes, bone marrow, cerebral spinal fluid, tissue, and urine. In a preferred aspect, the biological sample is peripheral blood. In other aspects, the blood is antecubital-vein blood, inferior-vena-cava blood or jugular-vein blood.

In aspects of the first through fourth embodiments, the cancer is one or more of a solid tumor, Stage I cancer, Stage II cancer, Stage III cancer, Stage IV cancer, epithelial cell cancer, breast cancer, prostate cancer, lung cancer, pancreatic cancer, and colorectal cancer.

In a fifth embodiment, the present invention is directed to methods for monitoring efficacy of a cancer treatment, comprising (a) determining the number of CAMLs in a biological sample from a subject before cancer treatment, and (b) comparing the number of CAMLs determined in (a) to a number of CAMLs determined from a similar biological sample from the same subject at one or more time points after treatment. In certain aspects, the methods further comprise (c) determining the number of CTCs in the biological sample of (a), and (d) comparing the number of CTCs determined in (c) to a number of CTCs determined from the biological sample of (b).

In aspects of the fifth embodiment, a change in the number of CAMLs is an indication of treatment efficacy, where the change is an increase or a decrease in the number of CAMLs.

In aspects of the fifth embodiment, the cancer treatment is chemotherapy or radiation therapy.

In aspects of the fifth embodiment, the number of CAMLs is determined using one or more means selected from the group consisting of size exclusion methodology, red blood cell lysis, FICOLL, a microfluidic chip, and flow cytometry, or a combination thereof. In a particular aspect, the size exclusion methodology comprises use of a microfilter. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution. In a particular aspect, the number of CAMLs is determined using a microfluidic chip based on physical size-based sorting, hydrodynamic size-based sorting, grouping, trapping, immunocapture, concentrating large cells, or eliminating small cells based on size. In a particular aspect, the number of CAMLs is determined using a CellSieve™ low-pressure microfiltration assay.

In certain aspects of the fifth embodiment, the numbers of CAMLs and CTCs are determined simultaneously using a microfilter. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution.

In aspects of the fifth embodiment, the biological sample is one or more selected from the group consisting of peripheral blood, blood, lymph nodes, bone marrow, cerebral spinal fluid, tissue, and urine. In a preferred aspect, the biological sample is peripheral blood. In other aspects, the blood is antecubital-vein blood, inferior-vena-cava blood or jugular-vein blood In aspects of the fifth embodiment, the cancer is one or more of a solid tumor, Stage I cancer, Stage II cancer, Stage III cancer, Stage IV cancer, epithelial cell cancer, breast cancer, prostate cancer, lung cancer, pancreatic cancer, and colorectal cancer.

In a sixth embodiment, the present invention is directed to an isolated circulating cancer associated macrophage-like cell (CAML), wherein the cell has the following characteristics: (a) large atypical nucleus having a size of about 14-64 µm; (b) expression of one or more of cytokeratin 8, 18 and 19, wherein the cytokeratin is diffused, or associated with vacuoles and/or ingested material; (c) cell size ranging from about 20 micron to about 300 microns; (d) morphological shape selected from the group consisting of spindle, tadpole, round, oblong, and amorphous; and (e) CD45 positive phenotype. In one aspect of this embodiment, the cell has one or more of the following additional characteristics: (f) expression of diffuse EpCAM with nearly uniform distribution; (g) expression of one or more markers of a primary tumor; (h) expression of monocytic CD11C and CD14 markers; and (i) expression of endothelial CD146, CD202b, and CD31 markers. In a particular aspect, the cell has each of the additional characteristics (f)-(i).

In a seventh embodiment, the present invention is directed to an isolated pathologically-definable circulating tumor cell (CTC), wherein the cell has one or more of the following characteristics: (a) cancer-like nucleus; (b) expression of one or more of cytokeratin 8, 18 and 19, and wherein the cytokeratins have filamentous pattern; and (c) CD45 negative phenotype.

In an eighth embodiment, the present invention is directed to an isolated apoptotic circulating tumor cell (CTC), wherein the cell has one or more of the following characteristics: (a) cancer-like nucleus; (b) expression of one or more of cytokeratin 8, 18 and 19, and wherein the cytokeratin is fragmented in the form of spots; and (c) CD45 negative phenotype.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIGS. 8B, 8C and 8D are from breast cancer patients. FIGS. 8A, 8F and 8G are from pancreatic cancer patients. FIGS. 8E, 8H and 8I are from prostate cancer patients. The merged images are generated by DAPI, CK 8, 18 & 19, EpCAM and CD45 staining.

DETAILED DESCRIPTION

Figure 1:
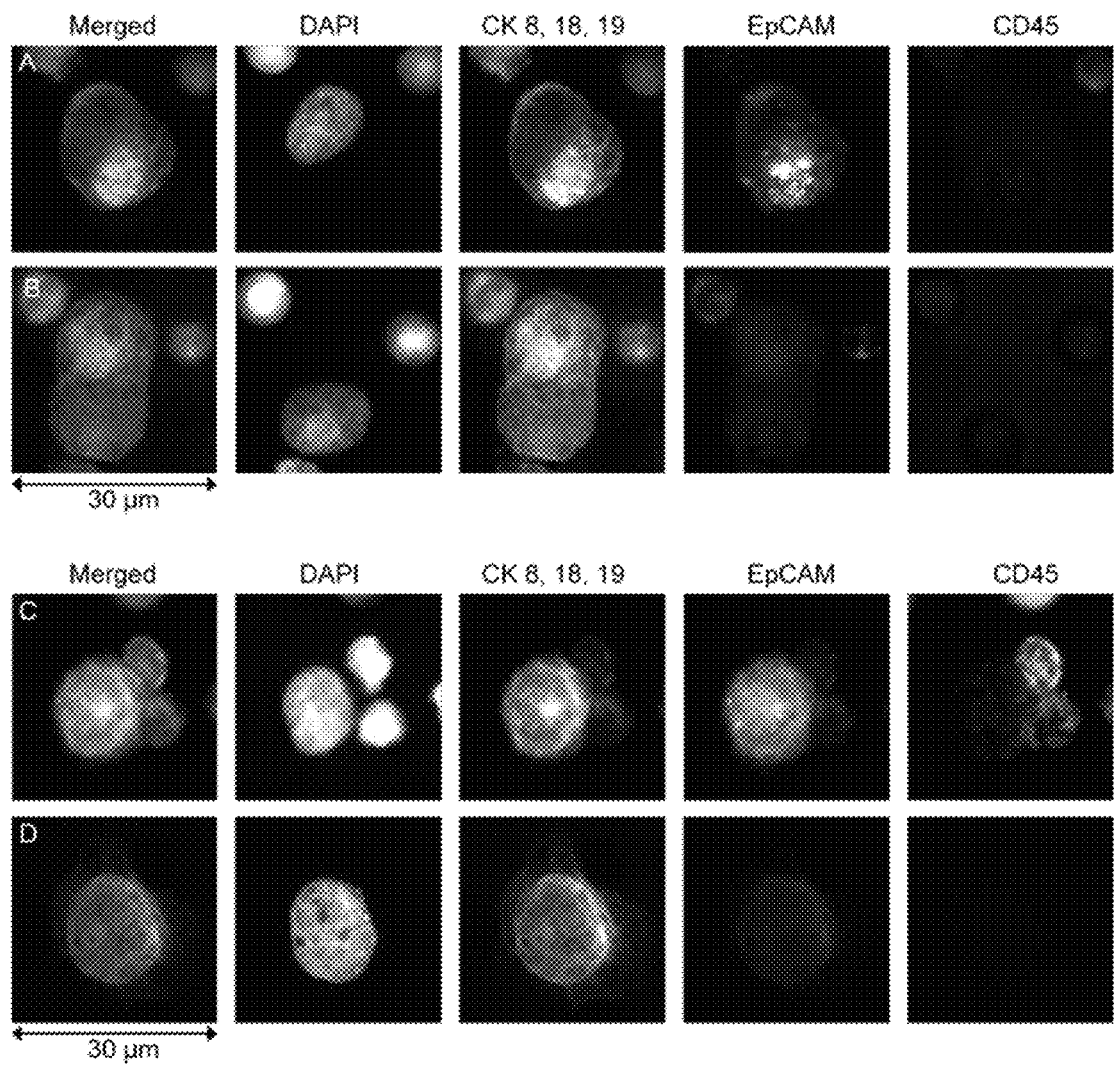
FIGS. 1A-1D shows circulating tumor cells found in blood of cancer patients. The merged images are generated by DAPI, CK 8, 18 & 19, EpCAM and CD45 staining.

The matters defined in the description such as a detailed construction and elements are nothing but the ones provided to assist in a comprehensive understanding of the invention. Accordingly, those of ordinary skill in the art will recognize that various changes and modifications of the embodiments described herein can be made without departing from the scope and spirit of the invention.

Cancer is the most feared illness in the world, affecting all populations and ethnicities in all countries. In the United States alone, there are more than 10 million cancer patients, with 1.5 million new cancer cases and almost 0.6 million deaths per year. Cancer death worldwide is estimated to be about 8 million annually, of which 3 million occur in developed countries where patients have available treatment.

Ideally there is a biomarker that can (i) provide early detection of all carcinomas, especially for at risk groups such as smokers for lung cancer, (ii) confirm other indications of cancer, such as high PSA for prostate cancer, and/or (iii) provide early detection of recurrence of cancer.

Oncologists need to know how best to treat newly diagnosed cancer patients. The current testing standard is a tissue biopsy, which is used to determine the cancer subtype, because therapeutic drugs are frequently effective only for specific subtypes. The biopsy method varies by location, but is invasive and can be risky.

To monitor treatment, oncologists need to know how well the drug is working for the patient, whether the dose should be adjusted, and whether the disease is spreading or in remission. The common methods for answering these questions are x-ray computed tomography (CT) scans and magnetic resonance imaging (Mills), both of which are expensive. Additionally, these methods cannot provide the necessary information until the tumor size has changed perceptibly.

Ninety percent of cancer patients die from metastasis, not from the primary tumor. The metastatic process involves tumor cells that break free of the primary carcinomas (solid tumors of epithelial cells) and enter the blood stream. These breakaway cancer cells are known as circulating tumor cells (CTCs). CTCs have the potential to be useful as a tool to determine therapy, monitor treatment, determine recurrence and provide prognostic information of survival. However, CTCs cannot be consistently collected from the blood even in stage III and IV cancers.

In this disclosure, a cell type is presented that is consistently found in the blood of carcinoma patients from stage I-IV. These cells are macrophage-like cells that contain the same tumor markers as the primary tumor and they are termed circulating Cancer Associated Macrophage-Like cells (CAMLs) herein.

CTCs and CAMLs can be found from the same patient sample at the same time by size exclusion methods, such as by microfiltration methods. Microfilters can be formed with pores big enough to let all red blood cells and majority of white blood cells through and retain larger cells such as CTCs and CAMLs. Size exclusion methods have also been implemented by microfluidic chips.

CAMLs have many clinical utilities when used alone. Furthermore, CAMLs can be combined with other markers such as CTCs, free DNA in blood and free proteins in blood to further improve sensitivity and specificity of a diagnosis. This is especially true for CAMLS and CTCs because they can be isolated and identified at the same time.

Circulating Tumor Cells

The CTCs express a number of cytokeratins (CKs). CK 8, 18, & 19 are the most commonly used in diagnostics, but surveying need not be limited to these three. The surface of solid tumor CTCs usually express epithelial cell adhesion molecule (EpCAM). However, this expression is not uniform or consistent. CTCs should not express any CD45, because it is a white blood cell marker. In assays to identify tumor associated cells, such as CTCs and CAMLs, it is sufficient to use antibody against CK 8, 18, or 19, or antibody against CD45 or DAPI. Combining the presence of staining with morphology, pathologically-definable CTCs, apoptotic CTCs and CAMLs can be identified.

FIGS. 1A-1D show four examples of pathologically-definable CTCs. A pathologically-definable CTC is identified by the following characteristics:

They have a "cancer-like" nucleus stained by DAPI. The exception is when the cell is in division; the nucleus is condensed.

They express at least CK 8, 18 and 19. The cytokeratins have a filamentous pattern.

They lack CD45 expression. To avoid missing low expressing CD45 cells, long exposure is used during image acquisition.

A pathologically-definable CTC of the present invention thus includes those CTCs having one, two or three of the following characteristics: (a) cancer-like nucleus; (b) expression of one or more of cytokeratin 8, 18 and 19, and wherein the cytokeratins have filamentous pattern; and (c) CD45 negative phenotype.

FIG. 1A shows a pathologically-definable prostate cancer CTC expressing well-defined EpCAM and FIG. 1B shows a pathologically-definable prostate cancer CTC expressing very low or no EpCAM. FIG. 1C shows a pathologically-definable breast cancer CTC expressing well-defined EpCAM and FIG. 1D shows a pathologically-definable breast cancer CTC expressing very low or no EpCAM.

FIGS. 2A-2D show examples of apoptotic CTCs. An apoptotic CTC is identified by the following characteristics:

They have a cancerous nucleus.

They express at least CK 8, 18 and 19; the cytokeratins are not filamented, but appear fragmented in the form of spots.

They do not express CD45.

An apoptotic CTC of the present invention thus includes those CTCs having one, two or three of the following characteristics: (a) cancer-like nucleus; (b) expression of one or more of cytokeratin 8, 18 and 19, and wherein the cytokeratin is fragmented in the form of spots; and (c) CD45 negative phenotype.

Figure 2:
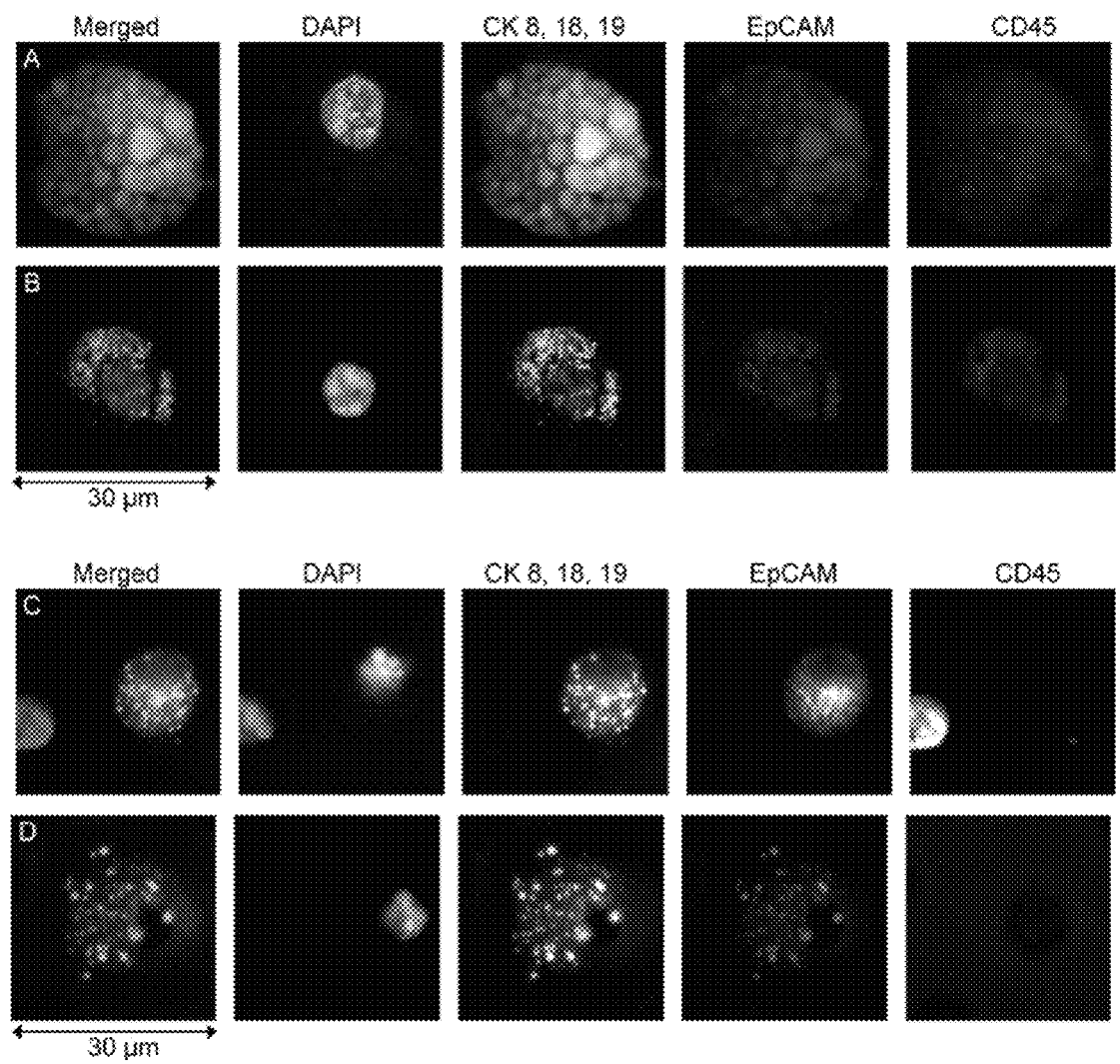
FIGS. 2A-2D shows apoptotic circulating tumor cells found in blood of cancer patients. The merged images are generated by DAPI, CK 8, 18 & 19, EpCAM and CD45 staining.

FIGS. 2A and 2B show apoptotic breast cancer CTCs expressing very low or no EpCAM at early and mid stages of apoptosis, respectively. FIGS. 2C and 2D show prostate cancer CTCs at mid stage of apoptosis expressing high and low EpCAM, respectively.

Circulating Cancer Associated Macrophage-Like Cells (CAMLs)

In the same patient samples, another type of cell was identified. This cell type has been termed a CAML. CAMLs have the following characteristics:

CAMLs have a large atypical nucleus; multiple individual nuclei can be found in CAMLs, though enlarged fused nucleoli approximately 14 µm to approximately 65 µm are common.

CAMLs may express at least CK 8, 18 or 19, and the CK is diffused, or associated with vacuoles and/or ingested material. CK is nearly uniform throughout the whole cell.

CAMLs are most of the time CD45 positive.

CAMLs are large, approximately 20 micron to approximately 300 micron in size.

CAMLs come in five distinct morphological shapes (spindle, tadpole, round, oblong, or amorphous).

Further analysis of CAMLs shows they also have the follow characteristics:

If CAML express EpCAM, EpCAM is diffused, or associated with vacuoles and/or ingested material, and nearly uniform throughout the whole cell, but not all CAML express EpCAM, because some tumors express very low or no EpCAM.

CAML express markers associated with the markers of the tumor origin; e.g., if the tumor is of prostate cancer origin and expresses PSMA, then CAML from this patient also expresses PSMA. Another example, if the primary tumor is of pancreatic origin and expresses PDX-1, then CAML from this patient also expresses PDX-1.

CAMLs express monocytic markers (e.g. CD11c, CD14) and endothelial markers (e.g. CD146, CD202b, CD31). CAMLs also have the ability to bind Fc fragments.

CAMLs of the present invention thus includes those CAMLs having one, two, three, four or five of the following characteristics: (a) large atypical nucleus having a size of about 14-64 µm; (b) expression of one or more of cytokeratin 8, 18 and 19, wherein the cytokeratin is diffused, or associated with vacuoles and/or ingested material; (c) cell size ranging from about 20 micron to about 300 microns; (d) morphological shape selected from the group consisting of spindle, tadpole, round, oblong, and amorphous; and (e) CD45 positive phenotype. CAMLs of the present invention also include those CAMLs having one, two, three or four of the following additional characteristics: (f) expression of diffuse EpCAM with nearly uniform distribution; (g) expression of one or more markers of a primary tumor; (h) expression of monocytic CD11C and CD14 markers; and (i) expression of endothelial CD146, CD202b, and CD31 markers. In a particular aspect, CAMLs of the present invention have each of the additional characteristics (f)-(i).

Figure 3:
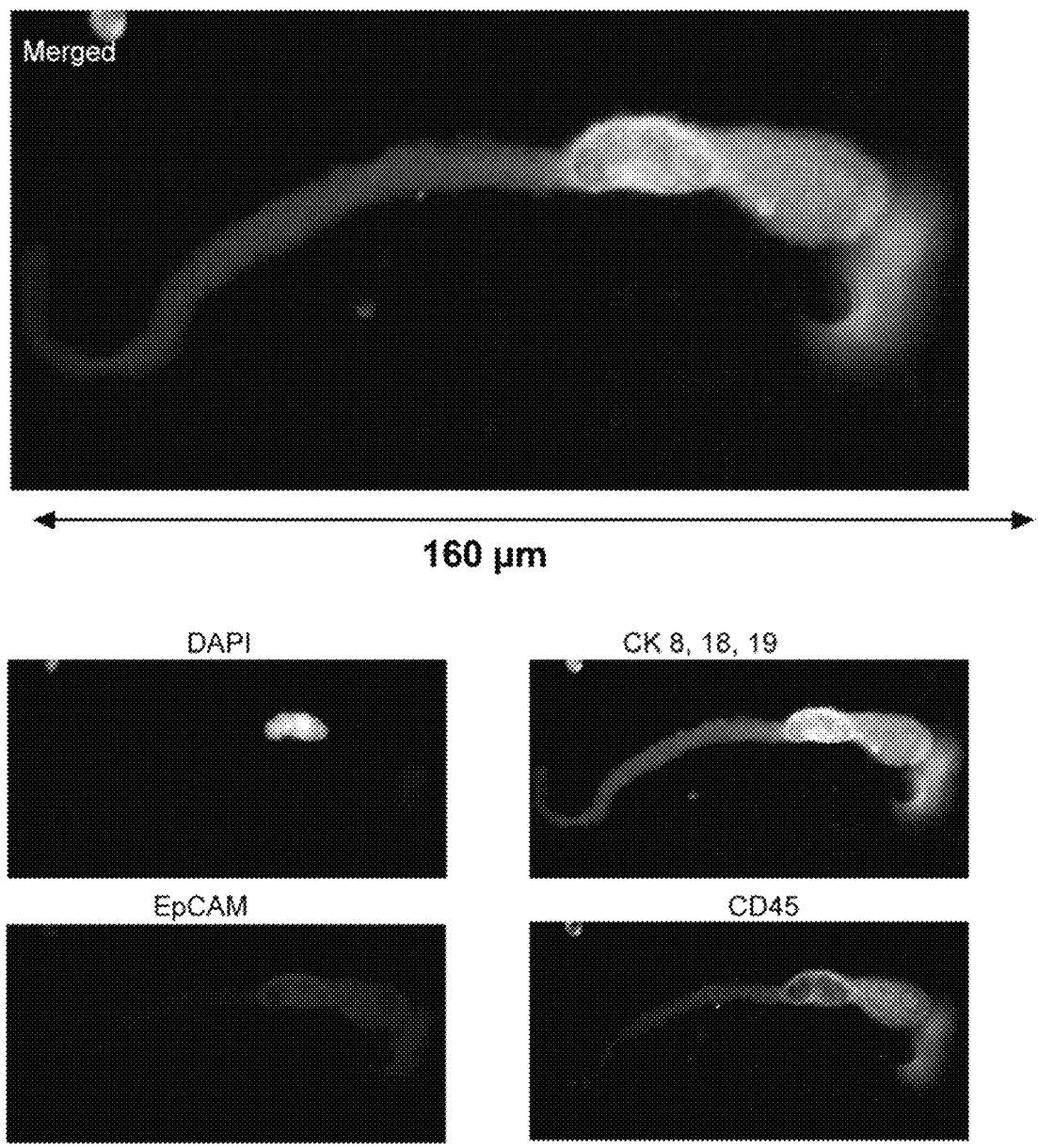
FIG. 3 shows a circulating cancer associated macrophage-like cell (CAML) found in the blood of cancer patients. This merged image is generated by DAPI, CK 8, 18 & 19, EpCAM and CD45 staining.
Figure 4:
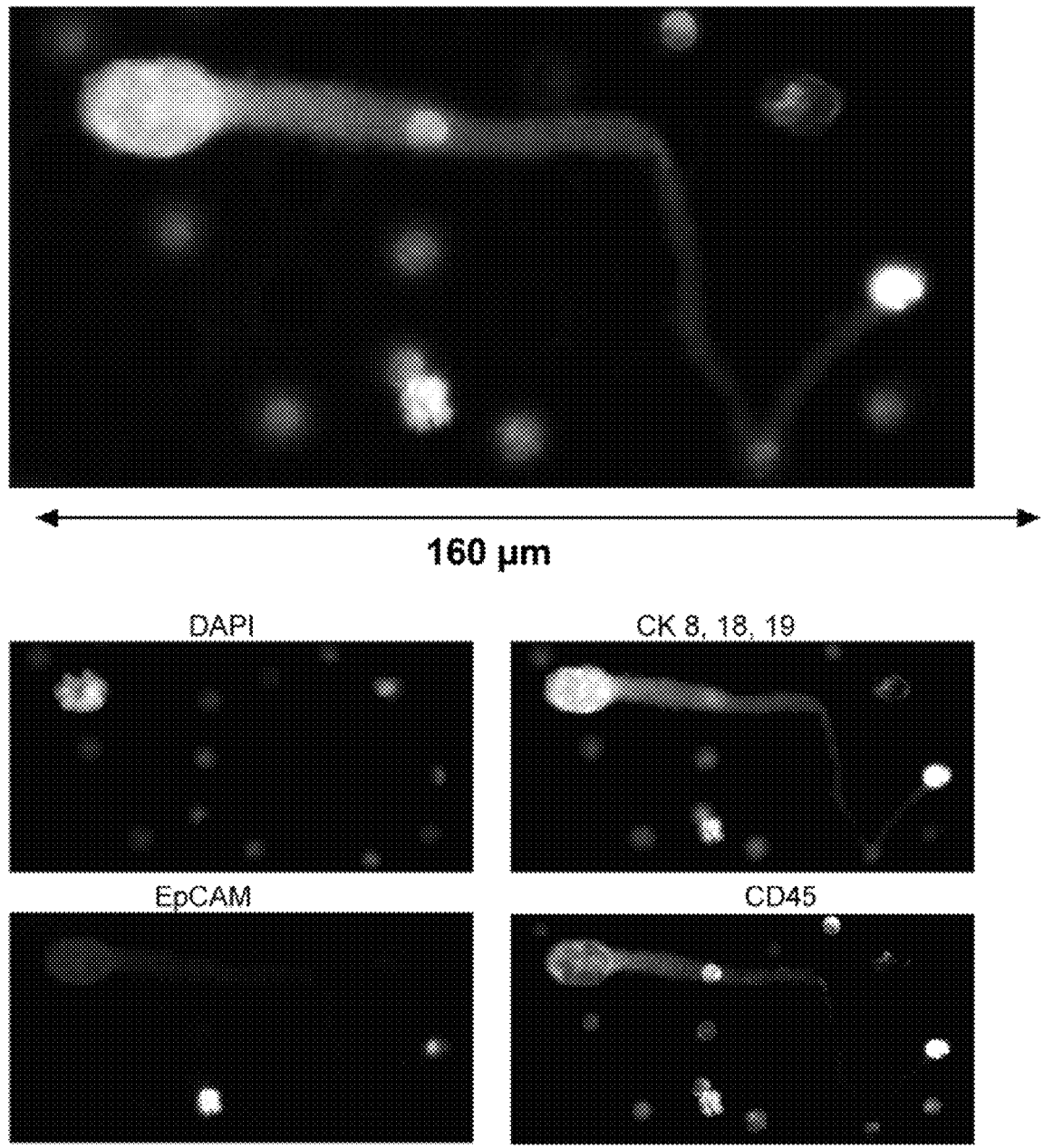
FIG. 4 shows a circulating cancer associated macrophage-like cell found in the blood of cancer patients. This merged image is generated by DAPI, CK 8, 18 & 19, EpCAM and CD45 staining.
Figure 5:
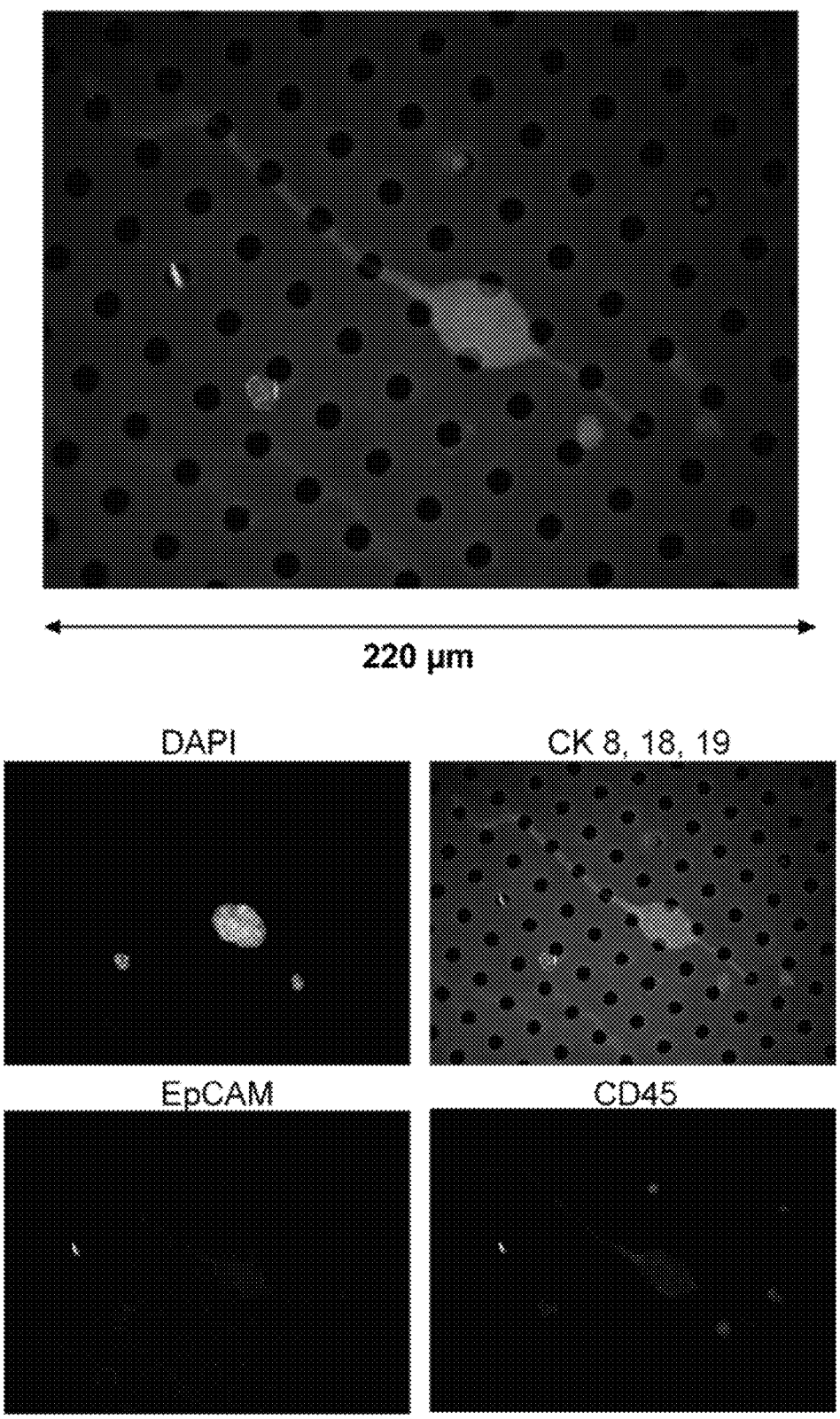
FIG. 5 shows a circulating cancer associated macrophage-like cell found in the blood of cancer patients. This merged image is generated by DAPI, CK 8, 18 & 19, EpCAM and CD45 staining.
Figure 6:
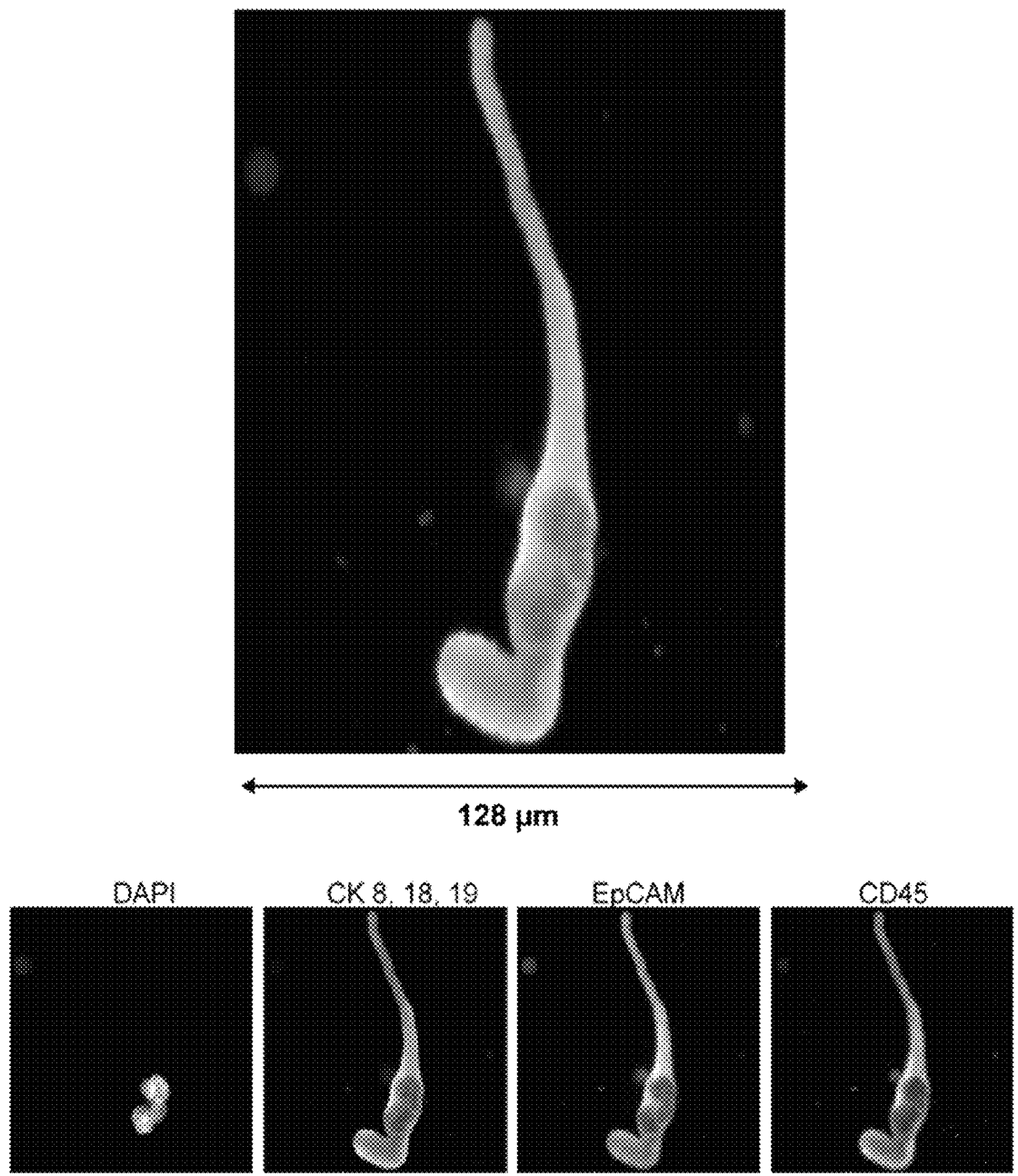
FIG. 6 shows a circulating cancer associated macrophage-like cell found in the blood of cancer patients. This merged image is generated by DAPI, CK 8, 18 & 19, EpCAM and CD45 staining.
Figure 7:
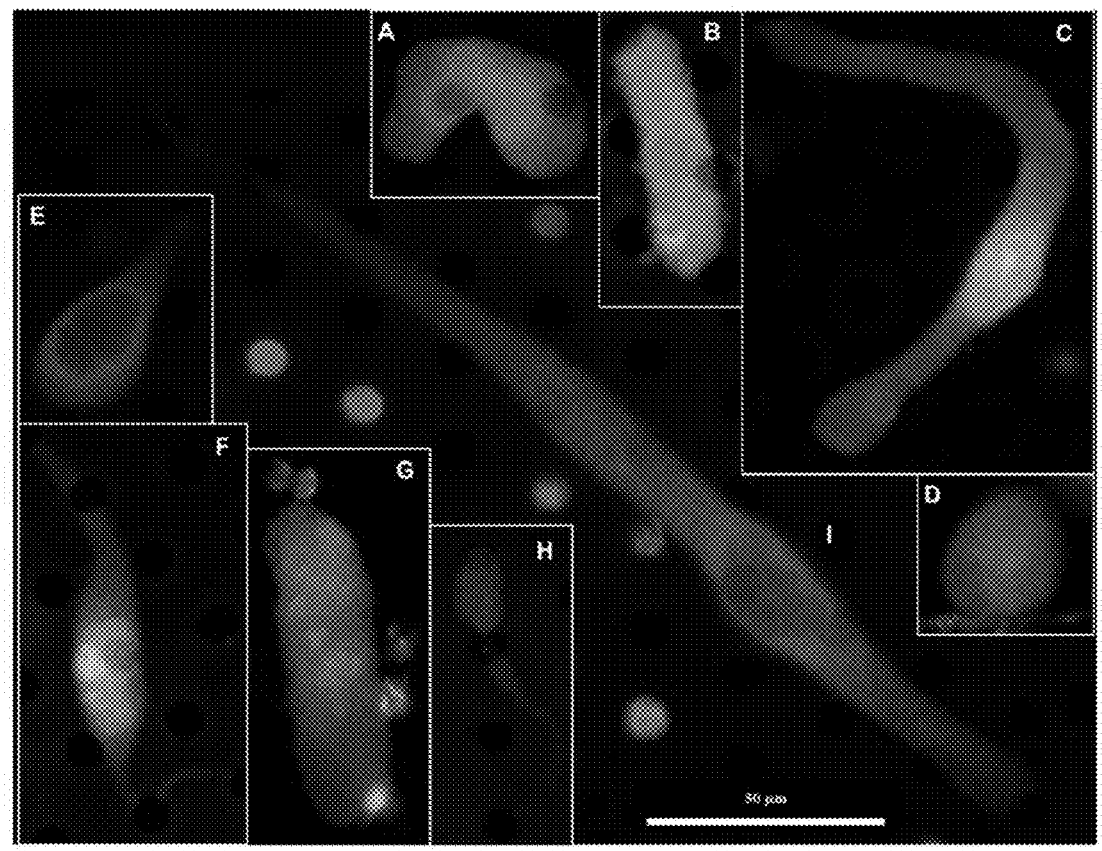
FIGS. 7A-7I show a gallery of circulating cancer associated macrophage-like cells found in the blood of cancer patients. These merged images are generated by DAPI, CK 8, 18 & 19, EpCAM and CD45 staining.
Figure 8A:
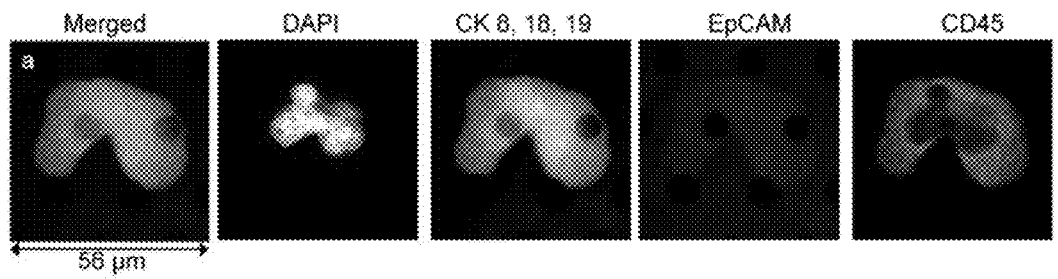
FIGS. 8A-8I show the expression of separate CK 8, 18, 19, EpCAM and CD45, and the nucleus, and the merged image of each of the cells in FIG. 7.
Figure 8B:
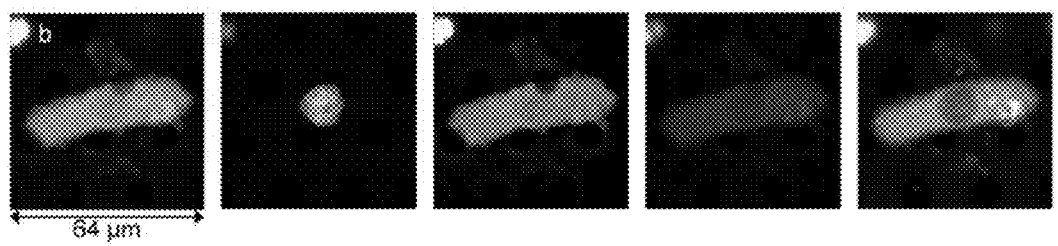
Figure 8C:
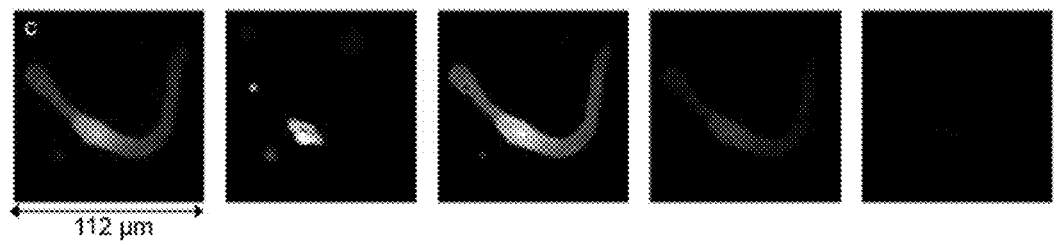
Figure 8D:
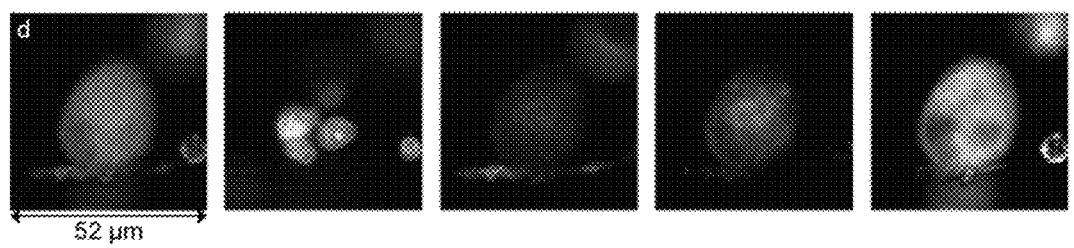
Figure 8E:
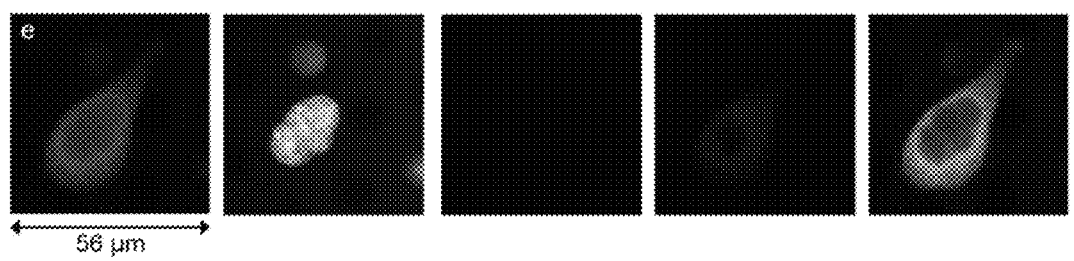
Figure 8F:
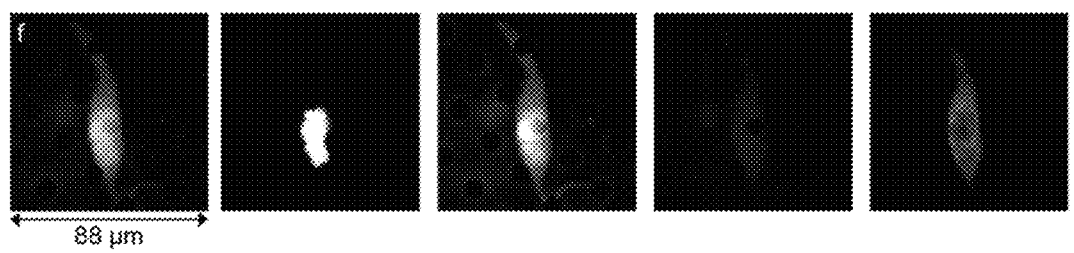
Figure 8G:
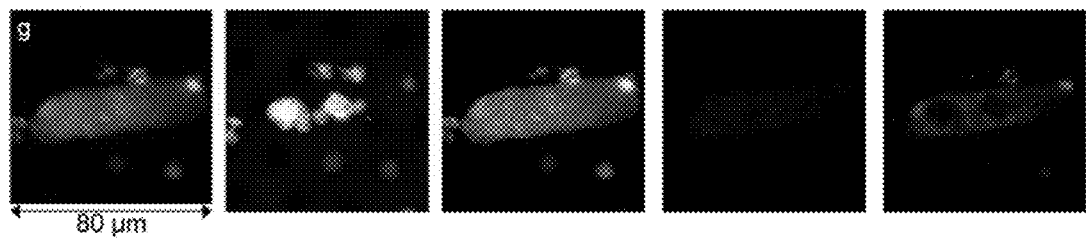
Figure 8H:
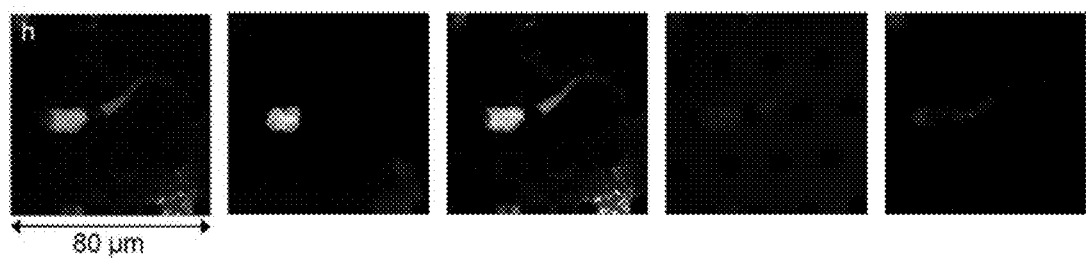
Figure 8I:
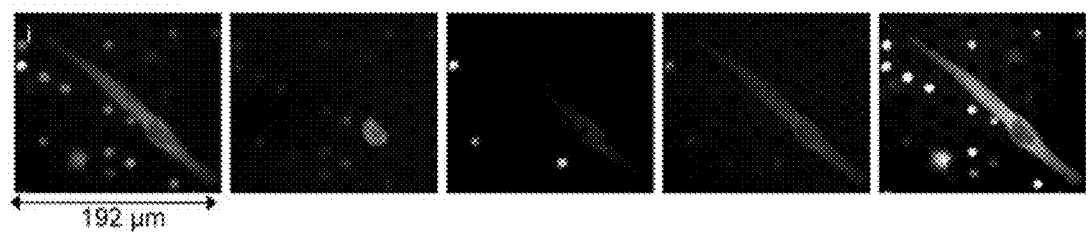

Images of CAMLs from a breast cancer patient are shown in FIGS. 3-5 and CAMLs from a prostate cancer patient are shown in FIG. 6. FIG. 7 contains a collage of CAMLs showing the five different CAML morphologies and signal variation from separate prostate, breast and pancreatic patient samples: (7A) pancreatic, (7B) breast, (7C) breast, (7D) breast (7E) prostate, (7F) pancreatic, (7G) pancreatic, (7H) prostate, and (7I) prostate. Examples of morphology variants are as follows: amorphous (7A), oblong (7B and 7G), spindle (3, 5, 6, 7C, 7F and 7I), round (7D) and tadpole (4, 7E & 7H). Color differences occur from varying degrees of protein expression from antibody reaction to EpCAM, cytokeratin and CD45. The expression of markers of each of the CAMLs in FIGS. 7A-I are shown in detail in FIGS. 8A-I.

Figure 9:
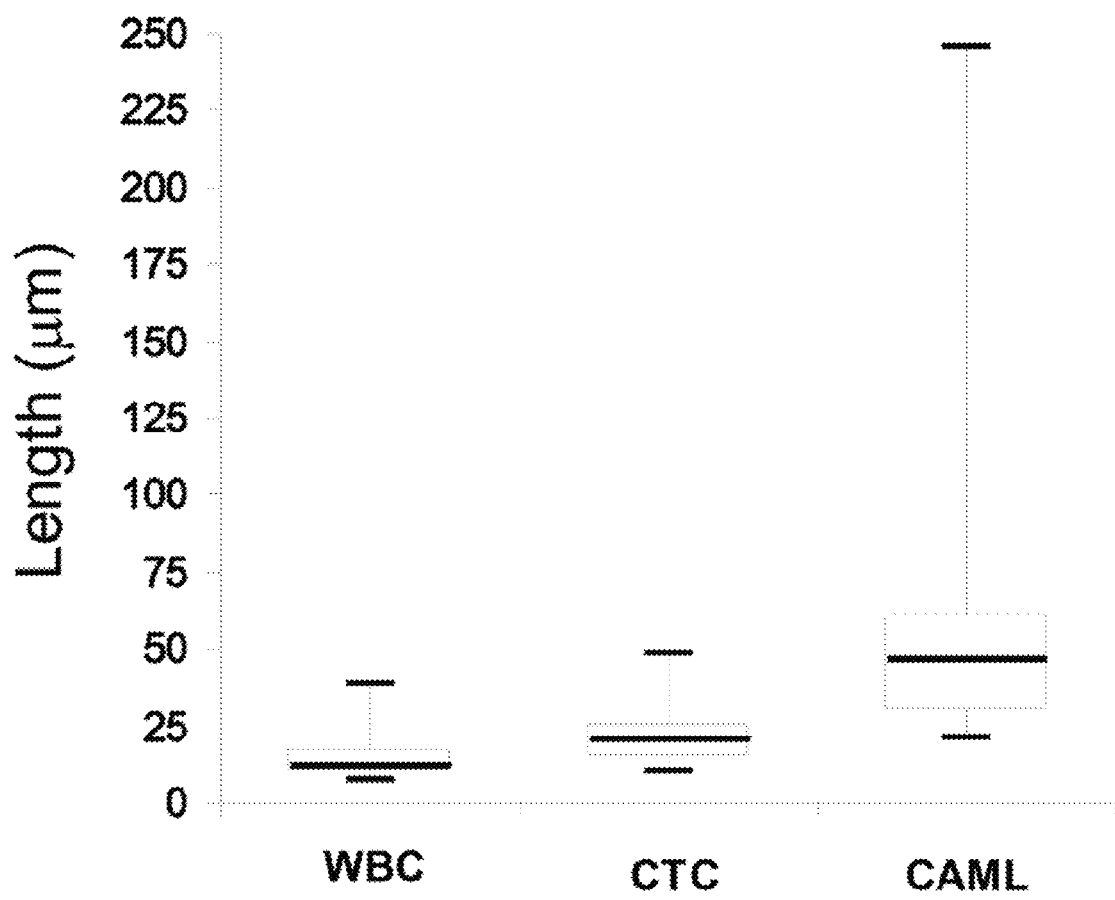
FIG. 9 is whisker plot of cytoplasmic diameters of white blood cells (WBCs), circulating tumor cells (CTCs) and circulating cancer associated macrophage-like cells (CAMLs).

FIG. 9 shows the whisker plot of cytoplasmic diameters of white blood cells (WBC), CTCs and CAMLs. The median size differences, and ranges, between WBC, CTCs and CAMLs captured on the microfilter from prostate, breast, and pancreatic (n=25 white blood cells, n=25 CAMLs and n=25 CTCs). Diameters were measured using the distance between the two longest points on the cell using Zen 2011 measurement software. The median value of white blood cells was 12.4 µm, CTCs was 18.8 µm and CAMLs was 43.5 µm.

Diagnostic Methods of Using CAMLs and CTCs

As suggested above, the unique characteristics of the CAMLs and CTCs described herein make them well-suited for use in clinical methodology including methods of screening and diagnosis diseases such as cancer, and in the monitoring of disease progression.

The invention is thus directed, in a first embodiment, to methods of screening a subject for cancer, comprising detecting circulating cancer associated macrophage-like cells (CAMLs) in a biological sample from a subject. In particular aspects, when CAMLs are detected in the biological sample, the subject is identified as potentially having a carcinoma or solid tumor. In other aspects, when CAMLs are detected in the biological sample, the subject is identified as having a carcinoma or solid tumor. In certain aspects, the methods encompassed by this embodiment also include detecting circulating tumor cells (CTCs) in the biological sample. In particular aspects of this first embodiment, the subject is a subject suspected of having cancer.

In a second embodiment, the invention is directed to methods for diagnosing cancer in a subject, comprising detecting CAMLs in a biological sample from a subject, wherein when CAMLs are detected in the biological sample, the subject is diagnosed with cancer. In certain aspects, the methods encompassed by this embodiment also include detecting CTCs in the biological sample, wherein when CAMLs and CTCs are detected in the biological sample, the subject is diagnosed with cancer.

In a third embodiment, the invention is directed to methods for detecting recurrence of cancer in a subject, comprising detecting CAMLs in a biological sample from a subject previously treated for cancer, wherein when CAMLs are detected in the biological sample, recurrence of cancer is detected. In certain aspects, the methods encompassed by this embodiment also include detecting CTCs in the biological sample, wherein when CAMLs and CTCs are detected in the biological sample, recurrence of cancer is detected.

In a fourth embodiment, the invention is directed to methods for confirming a diagnosis of cancer in a subject, comprising detecting CAMLs in a biological sample from a subject diagnosed with cancer, wherein when CAMLs are detected in the biological sample, a diagnosis of cancer is confirmed in the subject. In certain aspects, the methods encompassed by this embodiment also include detecting CTCs in the biological sample, wherein when CAMLs and CTCs are detected in the biological sample, a diagnosis of cancer is confirmed in the subject. In particular aspects, the initial cancer diagnosis is via mammography, PSA test, or presence of CA125. In a particular aspect, the subject is suspected of having cancer.

In each of these embodiments, CAMLs are detected using appropriate means which include, but are not limited to, one or more of size exclusion methodology, red blood cell lysis, FICOLL, a microfluidic chip, and flow cytometry, or a combination thereof. When size exclusion methodology is utilized, it may comprise the use of a microfilter. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution.

Alternatively, CAMLs may be detected using a microfluidic chip based on means that include, but are not limited to, physical size-based sorting, hydrodynamic size-based sorting, grouping, trapping, immunocapture, concentrating large cells, or eliminating small cells based on size.

In each of these embodiments, CTCs may also be detected along with CAMLs. Such detection may be simultaneously or sequential detection, and can utilize the same or different means. For example, simultaneous detection using a microfilter having a pore size that selects for both cell types may be used. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution.

The methods provided in these embodiments may be practiced using any biological sample suspected of containing CTCs and/or CAMLs. Suitable biological samples include, but are not limited to, one or more selected from the group consisting of peripheral blood, blood, lymph nodes, bone marrow, cerebral spinal fluid, tissue, and urine. In a preferred aspect, the biological sample is peripheral blood. In other aspects, the blood is antecubital-vein blood, inferior-vena-cava blood or jugular-vein blood.

The skilled artisan will appreciate that the methods provided in these embodiments are not limited to particular forms or types of cancer and that they may be practiced in association with a wide variety of cancers. Exemplary cancers include, but are not limited to, solid tumors, Stage I cancer, Stage II cancer, Stage III cancer, Stage IV cancer, epithelial cell cancer, breast cancer, prostate cancer, lung cancer, pancreatic cancer, and colorectal cancer.

Monitoring Treatment Efficacy Using CAMLs and CTCs

As suggested above, the unique characteristics of the CAMLs and CTCs described herein also make them well-suited for use in monitoring the effectiveness of disease treatments.

The present invention is thus directed, in a fifth embodiment, to methods for monitoring efficacy of a cancer treatment, comprising:

(a) determining the number of CAMLs in a biological sample from a subject before cancer treatment, and (b) comparing the number of CAMLs determined in (a) to a number of CAMLs determined from a similar biological sample from the same subject at one or more time points after treatment.

Given the prognostic capabilities associated with CTCs, the methods of this embodiment may further include the following additional steps:

(c) determining the number of CTCs in the biological sample of (a), and (d) comparing the number of CTCs determined in (c) to a number of CTCs determined from the biological sample of (b).

The skilled artisan will understand that a change in the number of CAMLs and/or CTCs will be an indication of treatment efficacy, where the change may be an increase or a decrease in the number of CAMLs and/or CTCs.

The particular cancer treatment is not limited by this method, but will generally comprise chemotherapy and/or radiation therapy.

These methods can be practiced by determining number of CAMLs using one or more means selected from the group consisting of size exclusion methodology, red blood cell lysis, FICOLL, a microfluidic chip, and flow cytometry, or a combination thereof. When size exclusion methodology is used, it may comprise use of a microfilter. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution. In a particular aspect, the number of CAMLs is determined using a microfluidic chip based on means that include, but are not limited to, physical size-based sorting, hydrodynamic size-based sorting, grouping, trapping, immunocapture, concentrating large cells, or eliminating small cells based on size. In another particular aspect, the number of CAMLs is determined using a CellSieve™ low-pressure microfiltration assay.

When both are monitored, the numbers of CAMLs and CTCs may be determined sequential or simultaneously using the same means or different means. For example, simultaneous detection using a microfilter having a pore size that selects for both cell types may be used. Suitable microfilters can have a variety of pore sizes and shapes. Microfilters having pores of about 7-8 microns in size are acceptable, and include round and rectangular pore shapes. Microfilters having round pores of about 7-8 microns in size are especially optimal when polymeric microfilters are used. In a preferred aspect, the microfilter has precision pore geometry and uniform pore distribution.

The methods provided in this embodiment may be practiced using any biological sample suspected of containing CTCs and/or CAMLs. Suitable biological samples include, but are not limited to, one or more selected from the group consisting of peripheral blood, blood, lymph nodes, bone marrow, cerebral spinal fluid, tissue, and urine. In a preferred aspect, the biological sample is peripheral blood. In other aspects, the blood is antecubital-vein blood, inferior-venacava blood or jugular-vein blood The skilled artisan will appreciate that the methods provided in this embodiment are not limited to particular forms or types of cancer and that they may be practiced in association with a wide variety of cancers. Exemplary cancers include, but are not limited to, solid tumors, Stage I cancer, Stage II cancer, Stage III cancer, Stage IV cancer, epithelial cell cancer, breast cancer, prostate cancer, lung cancer, pancreatic cancer, and colorectal cancer.

Discussions of the Biology and Clinical Results of CAMLs

Tumor-associated macrophages (TAMs) are specialized differentiated macrophages found within most tumors, which can be used as prognostic indicators of either tumor invasiveness or tumor suppression. TAMs, recruited to the stroma from circulating monocytes, are required for tumor cell intravasation, migration, extravasation, and angiogenesis. Tumors attract monocytes via chemoattractants (MCP-1, CCL-2). In turn TAMs secrete cytokines, chemokines and growth factors (e.g. MMP-1, CXCL12) which stimulate tumor cells with the potential to become circulating tumor cells (CTCs). TAMs and tumor cells then migrate via the lymphatic system, or intravasate across intra-tumor capillary barriers into the peripheral circulation.

Pathological evidence detailing the initial dissemination steps of CTCs via a metastatic cascade remains inconclusive. Typically, a cancer cell dissemination cascade requires 3 steps: CTC separation from the tumor, movement away from the parent mass, and migration into the circulatory system. Though various theories explain select aspects of this cascade (endothelial progenitor cells, cancer mesenchymal stem cells, hybrid cancer cells, etc.), none completely explain all three processes. Recently, in vivo studies have shown that circulating monocytic cells are intricately involved in tumor cell invasiveness, motility, and metastatic potential. Interactions between myeloid lineage cells and tumor cells have been documented in patients and modeled in mice suggesting a pathway for intravasation, but the mechanism for the final dissemination step is yet to be established.

Here we describe the existence of CAMLs, a highly differentiated giant circulating (macrophage-like) cell isolated from the peripheral blood of breast, prostate, and pancreatic cancer patients, which we hypothesize could be a disseminated TAM (DTAM). We isolated this cell type using CellSieve™ microfilter (Creatv MicroTech) with precision pore dimensions and uniform distribution. CellSieve™ microfiltration of 7.5 ml of whole peripheral blood are performed under low pressure without damaging cells, allowing for histological identification of cellular morphology. We define this giant cell as a circulating Cancer Associated Macrophage-Like cell (CAML), as it exhibits a CD14+ expression, vacuoles of phagocytosed material, and found exclusively in cancer patients (FIGS. 3-7, and Table 1). We propose that this cell population, not found in healthy individuals, could serve as a robust cellular biomarker of a previously undefined innate immune response to cancer aggressiveness, and monitor chemotherapy- and radiation therapy-induced responses. Observations of these giant cells interacting with CTCs while in circulation supports evidence that a patient's innate immune response has an observable effect on the migration of CTCs. The TIE-2 positive markers expressed by these macrophages suggest a role of CAML as cellular initiators of neovascularization within tumor metastases. We have uncovered supporting in vivo evidence that CAMLs may play an associated role in the migration of CTCs in circulation.

Giant fused macrophages are a poorly understood cell found in a multitude of tissues. They are hybrids of multinucleated cells originating from myeloid lineage involved in numerous physiological and pathological processes, including phagocytosis of foreign and necrotic tissue, tissue reabsorption, and inflammation. We find that CAMLs are giant cells presenting with enlarged nuclei, CD45+ and exhibit diffused cytoplasmic staining characteristic of epithelial cells: cytokeratin 8, 18, 19, and epithelial cell adhesion molecule (EpCAM) (FIGS. 3-8). Multiple individual nuclei can be found in CAMLs, though large fused nucleoli (14-64

μm diameter) are common (FIGS. 3-8). CAML cytoplasm, defined by a cytokeratin border, range from 21-300 um in length and is found on the filter with five distinct morphological phenotypes (spindle, tadpole, round, oblong, or amorphous) (FIGS. 3-8).

Although identification of these cells is straightforward due to their extreme size, large nuclear profile, and cytoplasmic signature, they have highly heterogeneous phenotypes. The expression of cytokeratin, EpCAM and CD45 all vary from lack of expression to very intense expression (FIGS. 8A-8H). This heterogeneity is further indicated in the five cell structures, the size ranges, and the various nuclear profiles (FIGS. 8A-8H). High marker expression heterogeneity implies CAMLs represent either different stages along pathways of differentiation or are the product of nonspecific cellular engulfment with varying cell types. This is unsurprising as macrophages are a highly plastic cell type capable of differentiating into numerous cell phenotypes.

Figure 10:
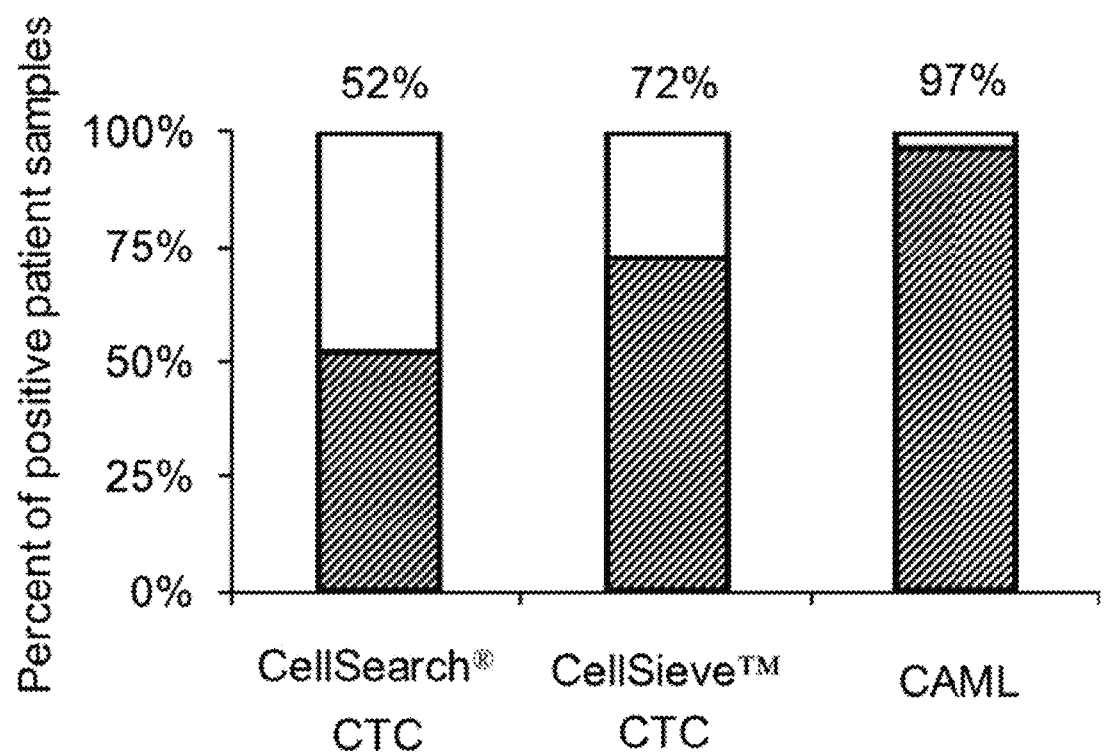
FIG. 10 is a comparison of presence of circulating tumor cells (CTCs) captured by CellSearch® and pathologically-definable CTCs isolated by CellSieve™ microfiltration and circulating cancer associated macrophage-like cells (CAMLs) isolated at the same time by Cell Sieve™ microfiltration.

Recognizing that CAMLs could serve as an independent prognostic indicator of cancer progression, similar to CTC enumeration, we compared the number of CAMLs and CTCs using the CellSieve™ low-pressure microfiltration assay (Creatv MicroTech, Inc) and the CellSearch® Circulating Tumor Cell test (Vendex, LLC). CTCs have been a challenge to isolate due to their rarity and limited occurrence (10-50%) in cancer patients with metastatic disease. TAM enumeration and phenotyping could have prognostic utility, but currently lacks sequential testing, tracking primary to metastatic progression, as this would require numerous invasive tumor biopsies. Enumeration of CTCs enriched by CellSearch® and CellSieve™ systems were directly compared to the enumeration of CAMLs isolated by CellSieve™ using blood from 29 cancer patients (FIG. 10). While CellSearch® uses EpCAM antibodies to enrich CTCs, CellSieve™ uses size exclusion. Both technologies phenotypically identify CTCs utilizing an antibody panel of anti-cytokeratin 8, 18, and 19, DAPI nuclear stain and absence of anti-CD45. Employing a CTC count of ≥1, the sensitivity of the CellSieve™ system was 72% [21 of 29 patients; breast=15/21 (71%), prostate=6/8 (75%)], while that of the CellSearch® system was 58% [15 of 29 patients; breast=9/21 (43%), prostate=6/8 (75%)]. CAML capture was positive in 97% (28 of 29) of samples tested (FIG. 10). Interestingly, the only CAML negative sample was a breast cancer patient being treated with bisphosphonates, a class of drugs, which inhibit formation of osteoclasts, a giant myeloid cell of the bone composed of fused cells. Thus, as the specificity of CAMLs is 100% for the samples tested, presence of CAML may provide a method for non-invasive sequential testing for use as a prognostic indicator of metastatic disease for a broad range of cancer patients.

Figure 11:
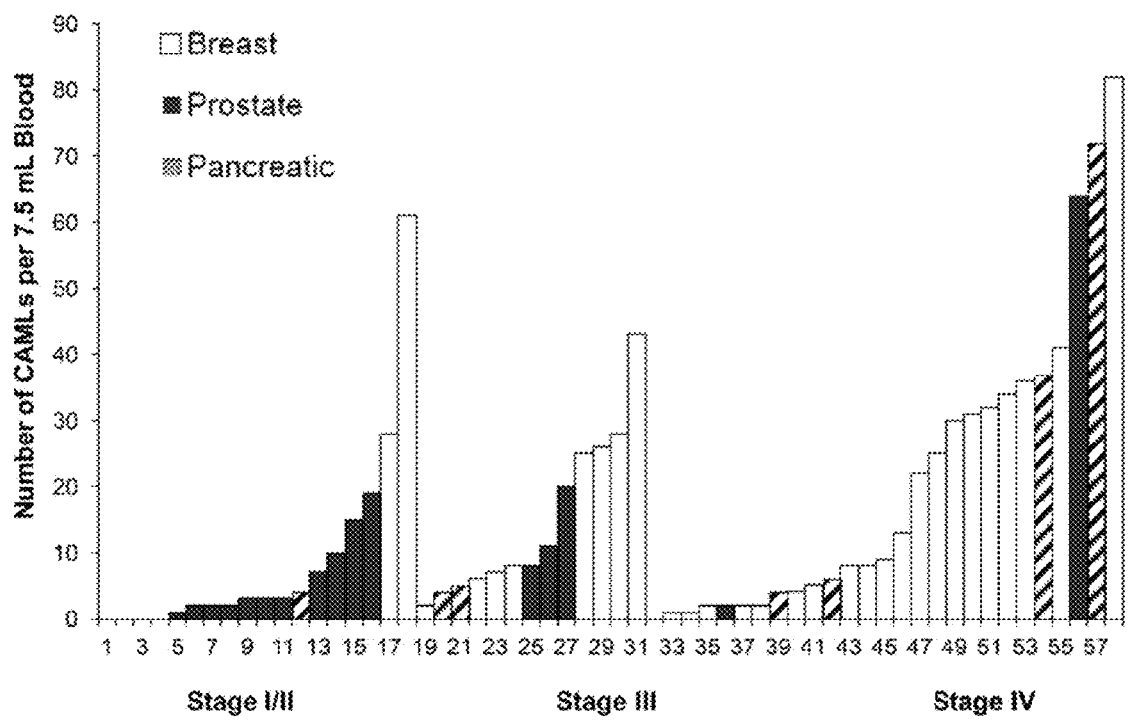
FIG. 11 is a plot of the number of circulating cancer associated macrophage-like cells (CAMLs) found in the circulation of breast, prostate, and pancreatic cancer patients in different stages of cancer.
Figure 12:
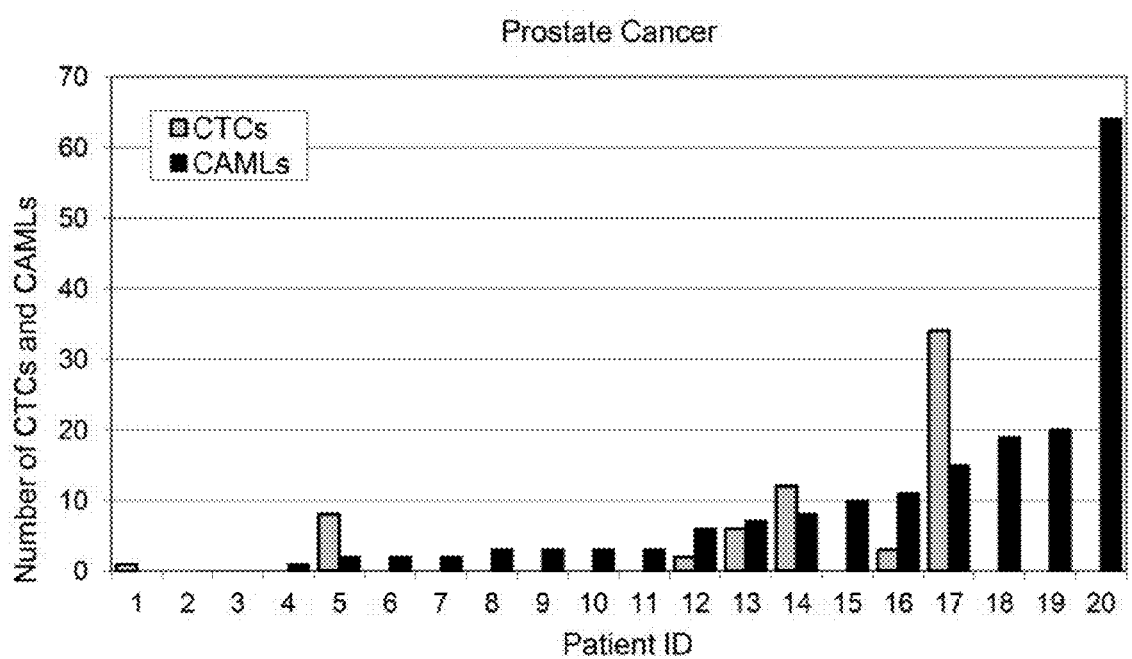
FIG. 12 is plot of number of CAMLs and CTCs found in the prostate cancer patient samples.
Figure 13:
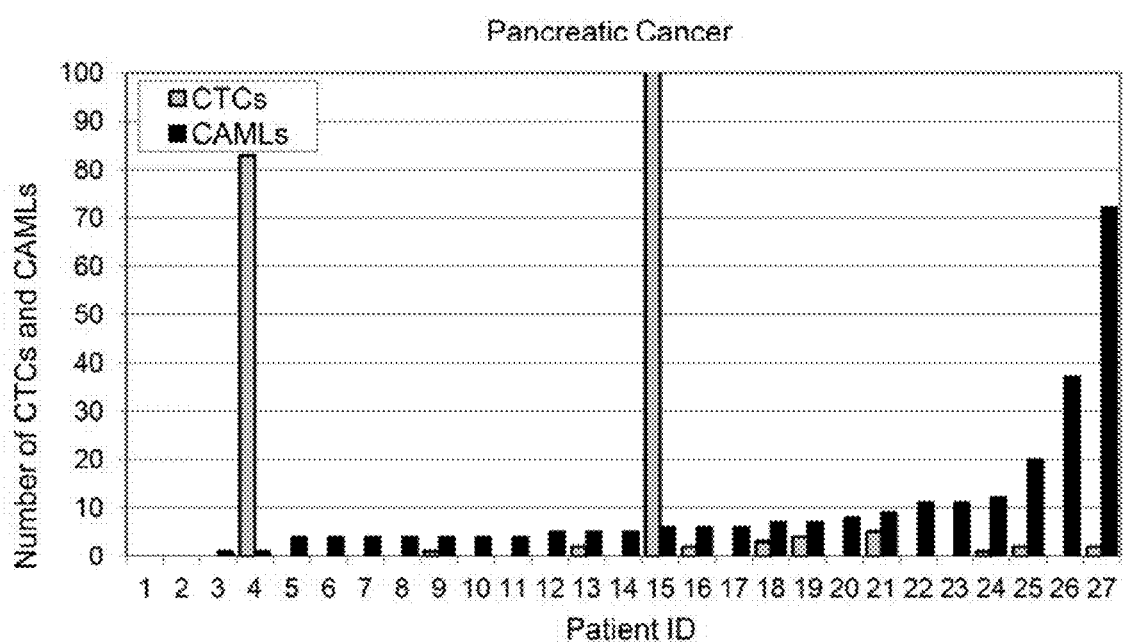
FIG. 13 is plot of number of CAMLs and CTCs found in the pancreatic cancer patient samples.
Figure 14:
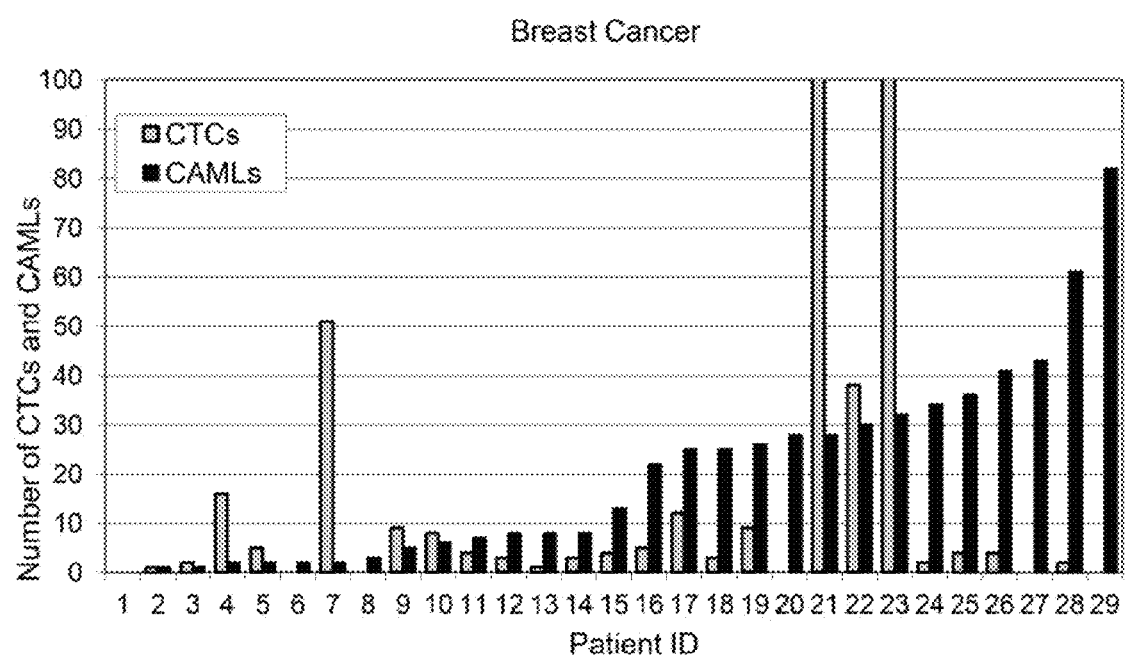
FIG. 14 is plot of number of CAMLs and CTCs found in the breast cancer patient samples.

To assess the sensitivity and specificity of CAMLs for applicability as a prognostic indication of metastatic disease, we examined samples from early to late stage cancer patients, and healthy subjects. Samples from 76 patients were run on CellSieve™ microfilters. The stage distribution included, Stage I (n=8), Stage II (n=9), Stage III (n=13), Stage IV (n=24), unknown stage (n=22) across three cancers: breast (n=29), pancreatic (n=27), and prostate (n=20) (Table S1). We included newly diagnosed and untreated patients (n=36) as well as patients undergoing non-surgical therapies (n=40) (Table 1). The study included healthy subjects (n=30), including two with benign disease, one fibroadenoma and one basal cell carcinoma. No CAMLs were found in this control group (Table 1). CAMLs were found in 97% (36 of 37) cancer patients with Stage III/IV cancer, 77% (13 of 17) of Stage I/II, and 93% (71 of 76) of all patients regardless of cancer type (FIG. 11). CAMLs were found in 85% (prostate) (FIG. 12), 93% (pancreatic) (FIG. 13), and 97% (breast) (FIG. 14) of the patients. CAMLs in prostate cancer samples were slightly lower in number, possibly due to the fact that 6 of 20 prostate patients were stage I. Although CTC analysis on microfilters provided an overall positivity of 54% across all patients tested, CAMLs provided 93% sensitivity across the same cohort (FIGS. 12-14 and Table 1). Though further study of patients with various illnesses must be assessed, these findings demonstrate that the presence CMALs could provide a robust and widely applicable assessment of cancer status.

TABLE 1

Summary of healthy subjects, CAML patient data and CTC patient data separated by stage, cancer type and therapy type. CTCs are found in a small percent of Stage I and II patients, while CAMLs are found in many stage I-IV patients. CTC numbers between the patients is highly variable with a standard deviation (SD) of >300%. CAMLs have a much lower SD, 110%, and whose numbers seem to correlate with stage and treatment.

| Subject | No. of patients | CAML positive (%) | Mean CAML ± SD | Median CAML | CAML range | CTC positive (%) | Mean CTC ± SD | Median CTC | CTC range |
|---|---|---|---|---|---|---|---|---|---|
| Healthy Normals | 28 | 0 | 0 ± 0 | 0 | 0-0 | 0 | 0 ± 0 | 0 | 0-0 |
| Nonmalignant | 2 | 0 | 0 ± 0 | 0 | 0-0 | 0 | 0 ± 0 | 0 | 0-0 |
| Stage I | 8 | 63 | 10.8 ± 20.9 | 3 | 0-61 | 38 | 4.6 ± 11.9 | 0 | 0-34 |
| Stage II | 9 | 89 | 8.0 ± 9.6 | 3 | 0-28 | 22 | 1.6 ± 3.1 | 0 | 0-28 |
| Stage III | 13 | 100 | 15.8 ± 12.5 | 9.5 | 2-43 | 62 | 13.3 ± 30.2 | 3.5 | 0-108 |
| Stage IV | 24 | 96 | 21.3 ± 23.8 | 8 | 0-82 | 75 | 57.2 ± 172.4 | 3 | 0-682 |
| Unknown | 22 | 95 | 6.2 ± 4.5 | 5.5 | 0-20 | 45 | 4.8 ± 17.5 | 0 | |
| Cancer Type | 76 | 93 | 13.4 ± 17.4 | 6 | 0-82 | 54 | 22.5 ± 100.3 | 1 | 0-682 |
| Breast (IBC) | 14 | 93 | 24.9 ± 24.0 | 23.5 | 0-82 | 71 | 11.4 ± 28.1 | 3 | 0-108 |
| Breast (IDC) | 8 | 100 | 15.9 ± 16.1 | 10.5 | 1-41 | 100 | 9.0 ± 17.0 | 3.5 | Jan-51 |
| Breast (unknown) | 7 | 100 | 15.0 ± 14.2 | 8 | 2-32 | 71 | 106.3 ± 254.2 | 5 | 0-682 |
| Prostate | 20 | 85 | 9.0 ± 14.3 | 3 | 0-64 | 35 | 3.3 ± 7.9 | 0 | 0-34 |
| Pancreatic | 27 | 93 | 9.5 ± 14.5 | 5 | 0-72 | 41 | 24.8 ± 106.5 | 0 | 0-541 |
| Therapy Type | 76 | | | | | | | | |
| No treatment | 36 | 86 | 4.4 ± 4.0 | 3.5 | 0-19 | 42 | 20.2 ± 92.0 | 0 | 0-541 |
| Hormone | 13 | 92 | 11.8 ± 16.7 | 8 | 0-64 | 69 | 6.2 ± 9.6 | 3 | 0-34 |
| Chemotherapy | 24 | 100 | 26.2 ± 21.9 | 27 | 2-82 | 58 | 8.9 ± 22.6 | 2 | 0-108 |
| Unknown | 3 | 100 | 26.3 ± 11.6 | 25 | 13-34 | 100 | 229.3 ± 392.0 | 4 | 2-682 |

Figure 15:
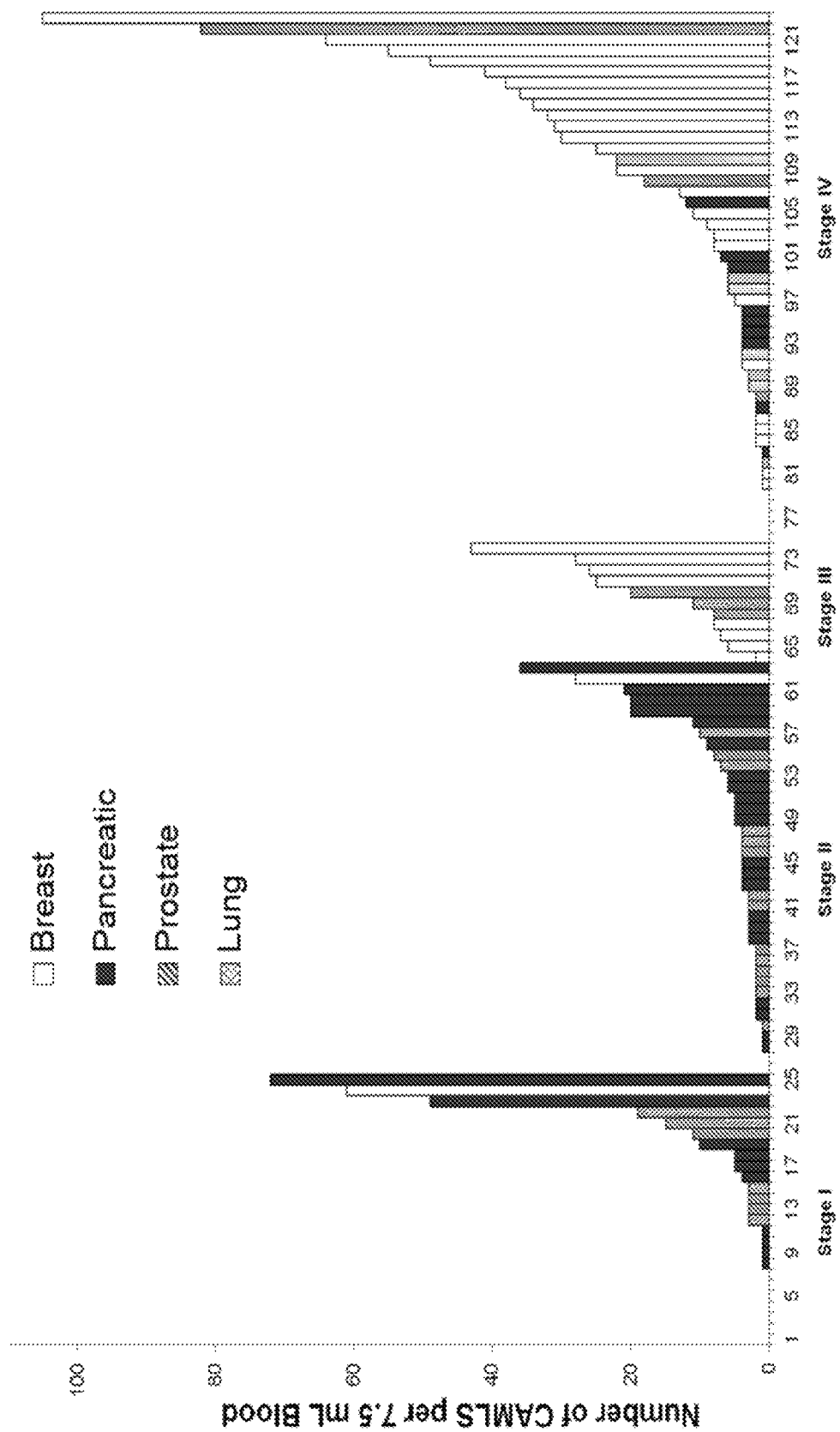
FIG. 15 is a plot of the number of circulating cancer associated macrophage-like cells (CAMLs) found in the circulation of breast, prostate, pancreatic and lung cancer patients in different stages of cancer.

As more samples were collected, additional CAML data was obtained. FIG. 15 presents CAML counts for 122 patients with staging information for breast, pancreatic, prostate and non-small cell lung cancer (NSCLC). For Stage I, one pancreatic cancer patient and six prostate cancer patients did not have any CAMLs. For Stage II, one pancreatic cancer patient and one prostate cancer patient did not have any CAMLs. For Stage IV, one breast cancer patient, one lung cancer patient and three pancreatic cancer patients did not have any CAMLs.

Figure 16A:
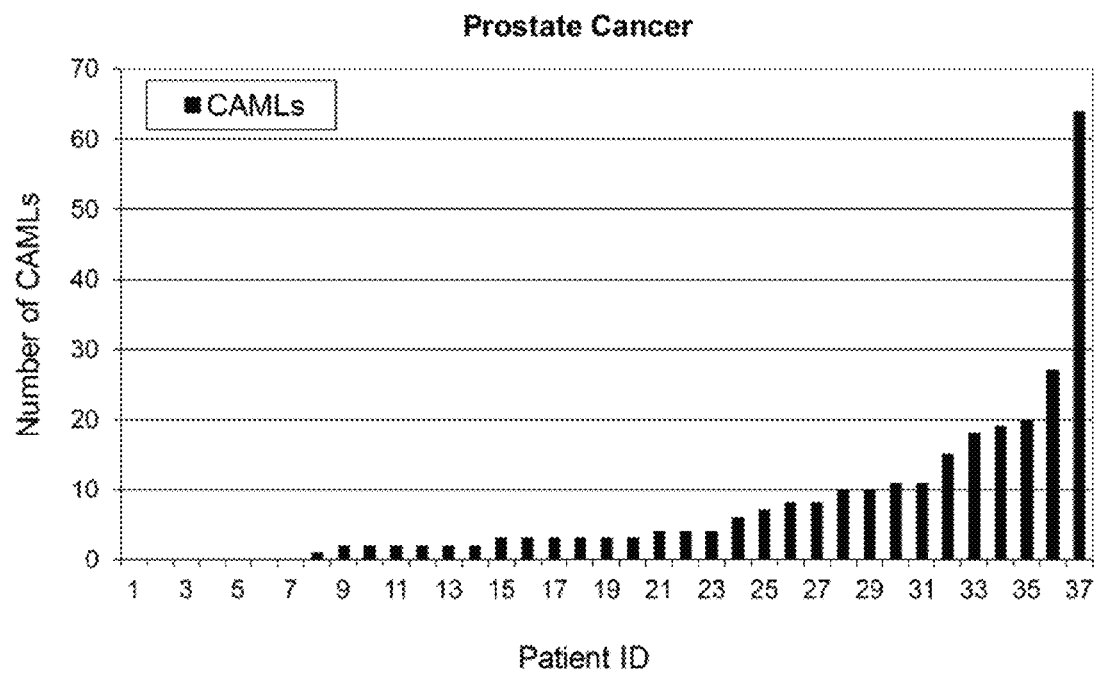
FIGS. 16A and 16B are plots of number of CAMLs and CTCs found in the prostate cancer patient samples, respectively.
Figure 16B:
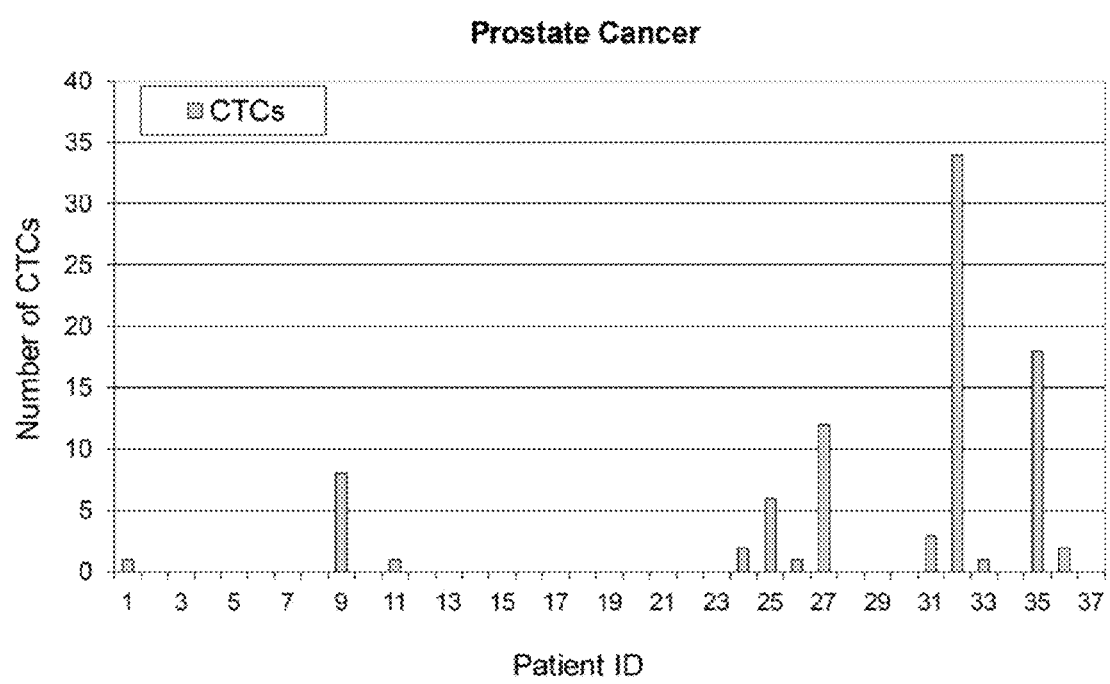

FIGS. 16A and 16B present numbers of CAMLs and CTCs from prostate cancer patient data obtained to date, respectively. Staging information was not known for all patients. The percentage of prostate cancer patients with CAMLs was 81% (30/37) (FIG. 16A), where 13 are known as Stage I. The percentage of prostate cancer patients with pathologically-definable CTCs was 32% (12/37) (FIG. 16B).

Figure 17A:
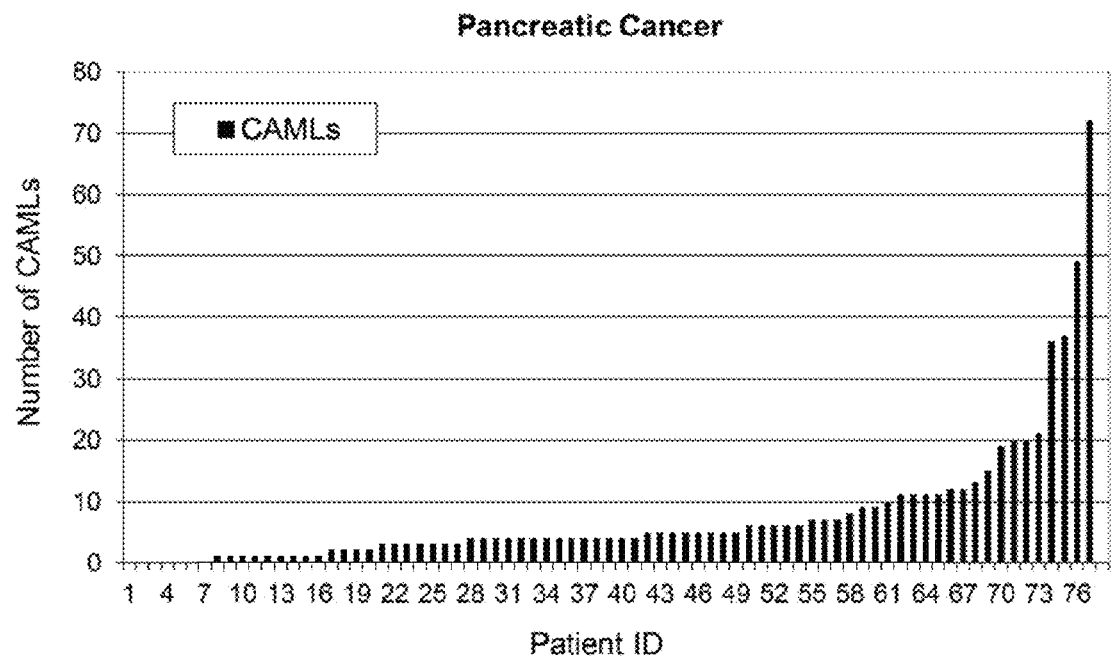
FIGS. 17A and 17B are plot of number of CAMLs and CTCs found in the pancreatic cancer patient samples, respectively.
Figure 17B:
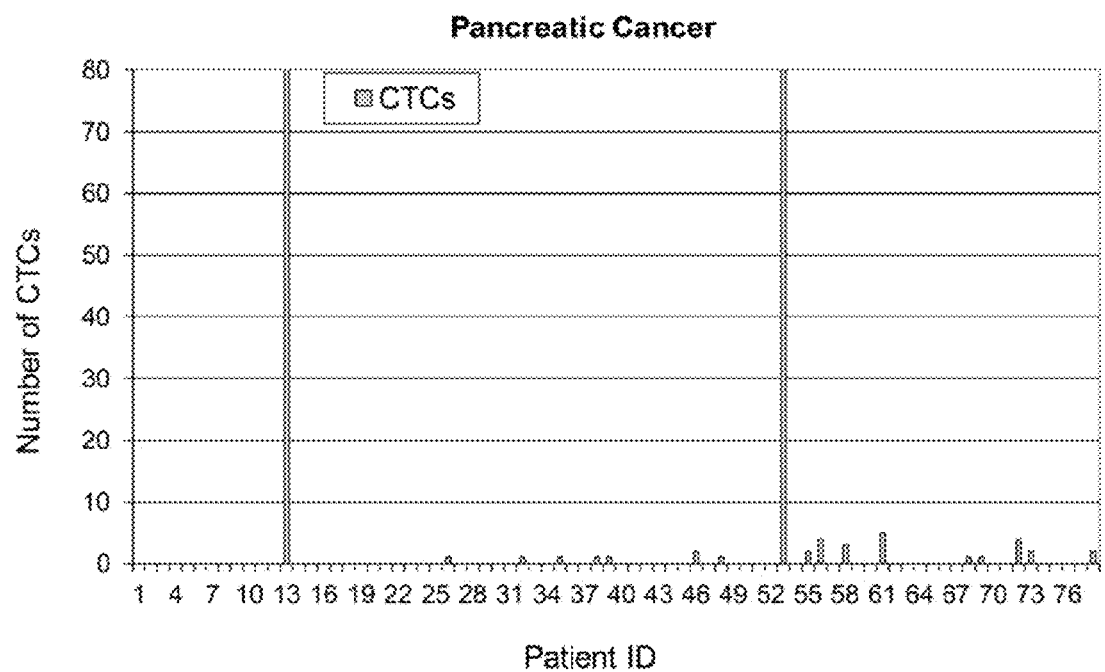

FIGS. 17A and 17B present numbers of CAMLs and CTCs from pancreatic cancer patient data obtained to date, respectively. Staging information was not known for all patients. The percentage of pancreatic cancer patients with CAMLs was 93% (71/76) (FIG. 17A), where 11 were known as Stage I. Two samples had pathologically-definable CTCs larger than 80. Samples No. 13 and 53 had 83 and 541 pathologically-definable CTCs, respectively. The percentage of prostate cancer patients with pathologically-definable CTCs was 23% (18/76) (FIG. 17B).

Figure 18A:
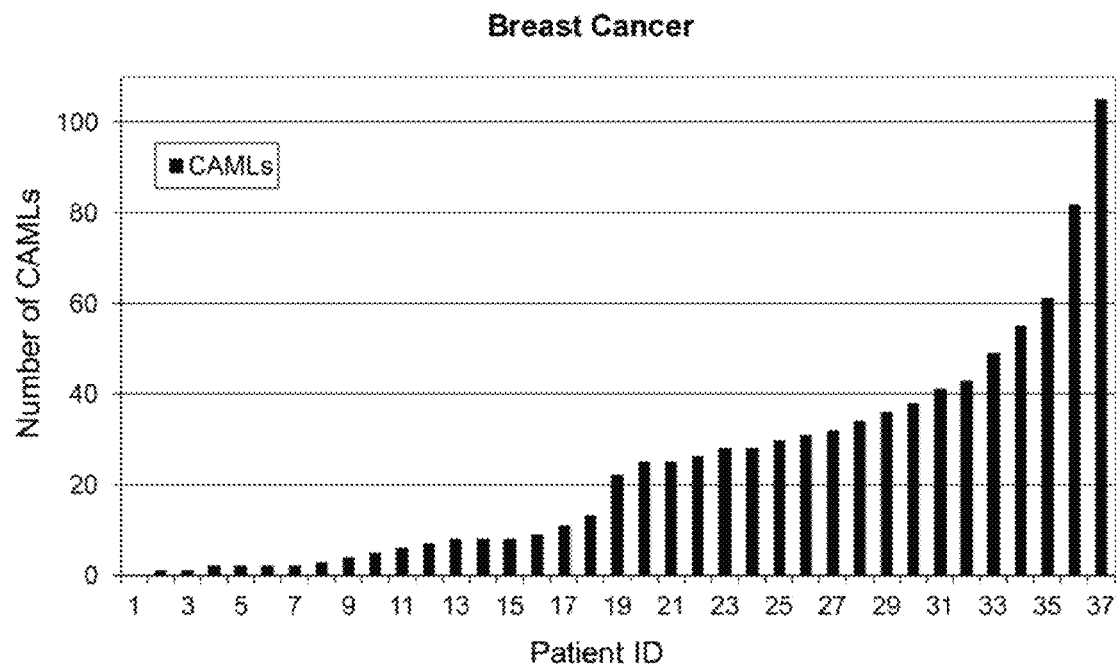
FIGS. 18A and 18B are plot of number of CAMLs and CTCs found in the breast cancer patient samples, respectively.
Figure 18B:
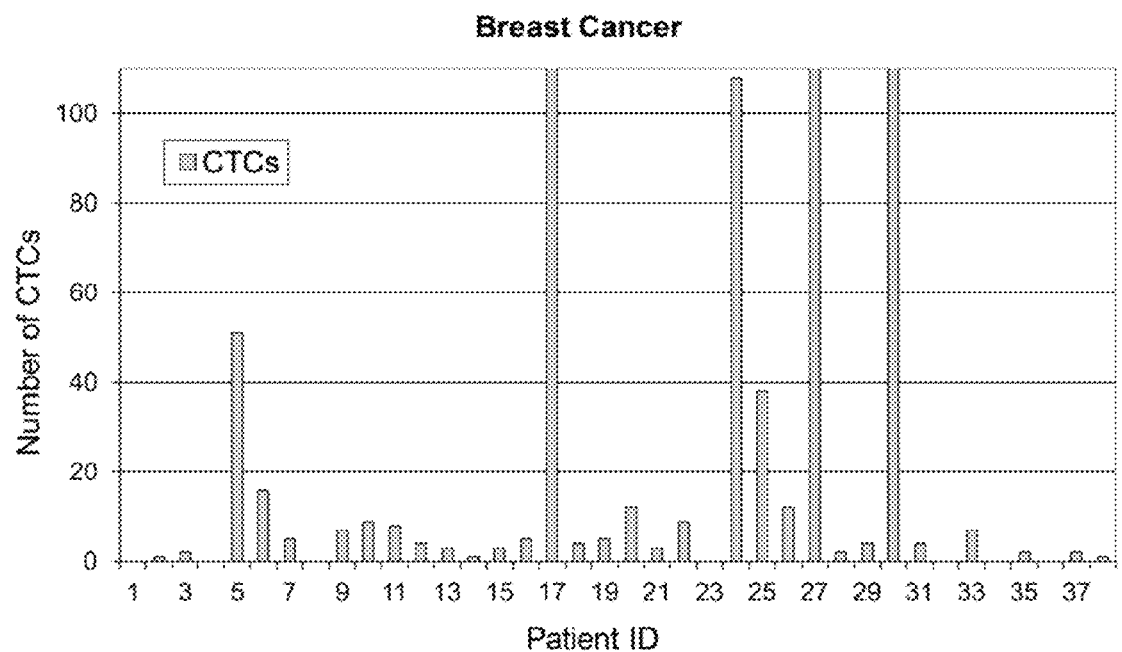

FIGS. 18A and 18B present numbers of CAMLs and CTCs from breast cancer patient data obtained to date, respectively. Staging information was not known for all patients. The percentage of breast cancer patients with CAMLs was 97% (36/37) (FIG. 18A), where only one was known as Stage I. One Stage IV patient did not have any CAML because she was taking the bisphosphonates. Four samples had pathologically-definable CTCs larger than 110. Samples No. 17, 27 and 30 had 978, 682 and 707 pathologically-definable CTCs, respectively. The percentage of breast cancer patients with pathologically-definable CTCs was 84% (31/37) (FIG. 18B).

Figure 19:
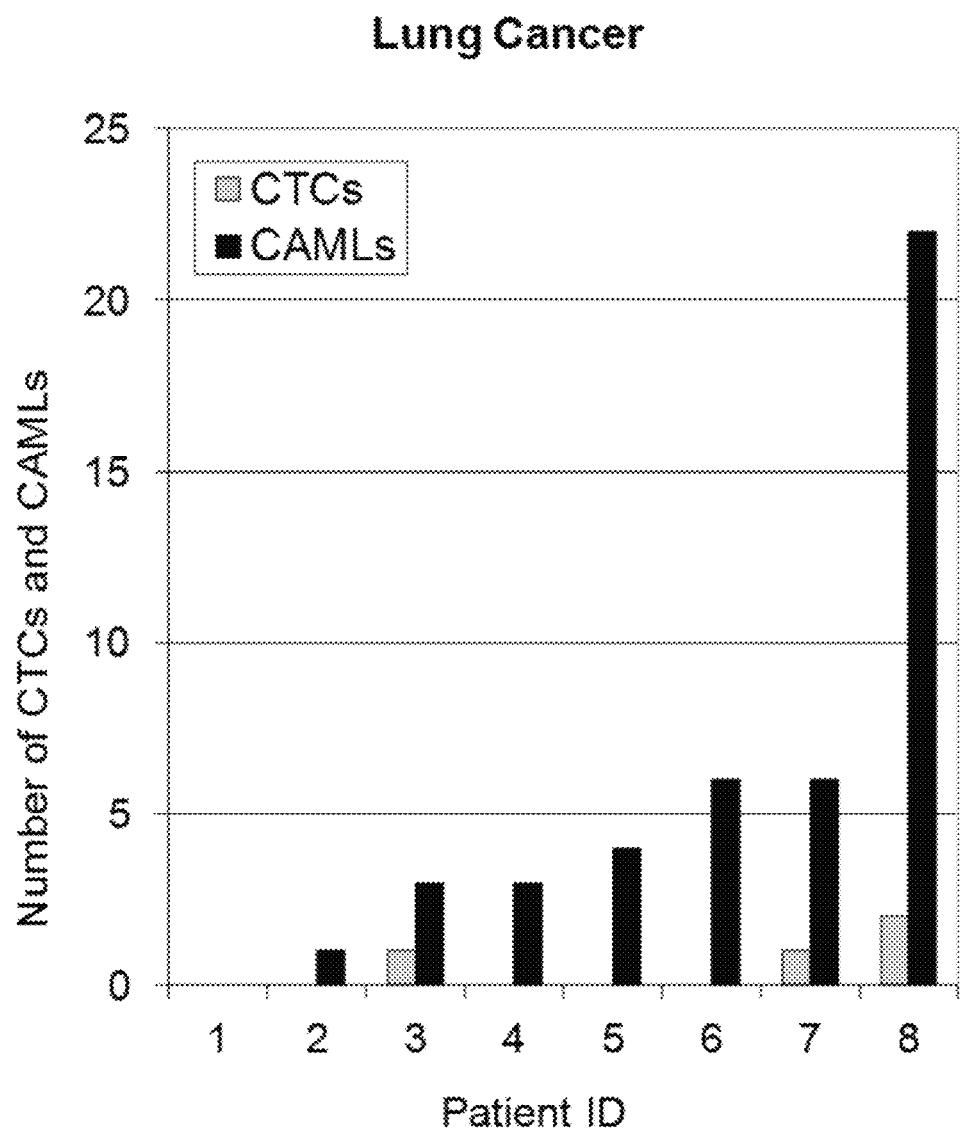
FIG. 19 is plot of number of CAMLs and CTCs found in the lung cancer patients.

FIG. 19 presents numbers of CAMLs and CTCs from NSCLC patient data obtained to date. Staging information was not known for all patients. The percentage of NSCLC patients with CAMLs was 88% (7/8). The percentage of NSCLC patients with pathologically-definable CTCs was 38% (3/8).

Figure 20:
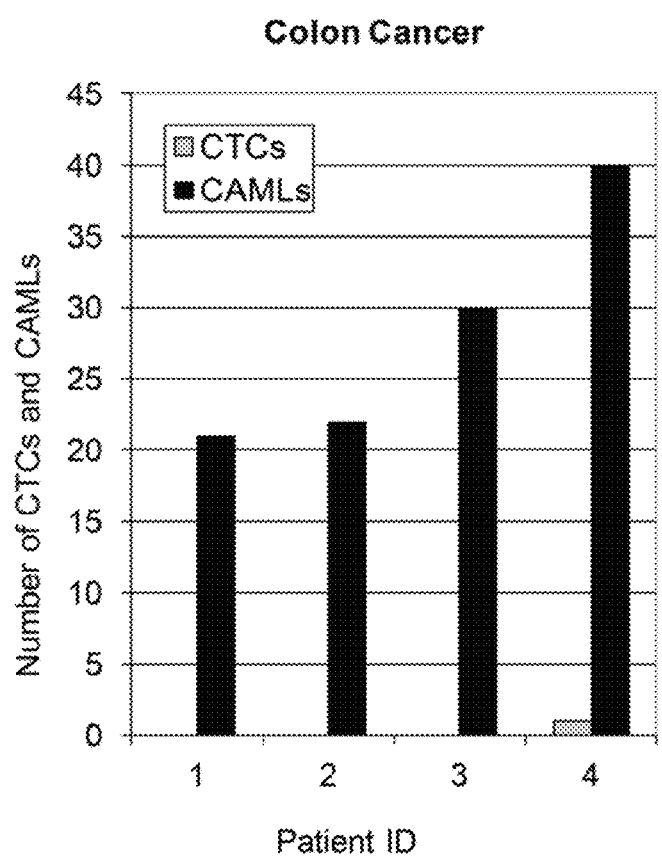
FIG. 20 is plot of number of CAMLs and CTCs found in the colorectal cancer patients.

FIG. 20 presents numbers of CAMLs and CTCs from colorectal cancer patient data obtained to date. All the patients were Stage IV. The percentage of colorectal cancer patients with CAMLs was 100% (4/4) for this small sample size. The percentage of colorectal cancer patients with pathologically-definable CTCs was 25% (1/4).

In all these data, the CAMLs were found in much larger number of the patients than CTCs.

Though further study of patients with various illnesses must be assessed, these findings demonstrate that the presence CAMLs provides a robust and widely applicable assessment of cancer status for carcinomas.

Figure 21:
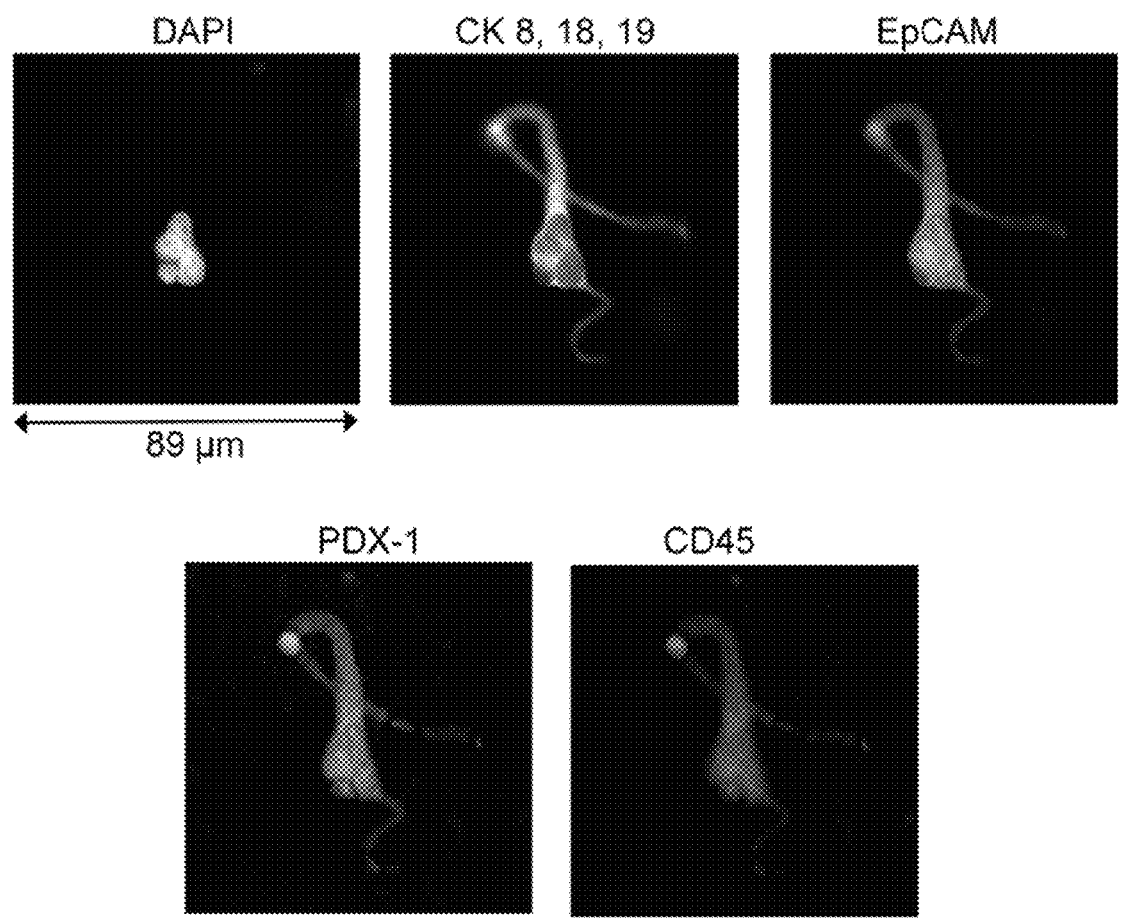
FIG. 21 is an example of a CAML from a pancreatic cancer patient also stained for PDX-1.
Figure 22:
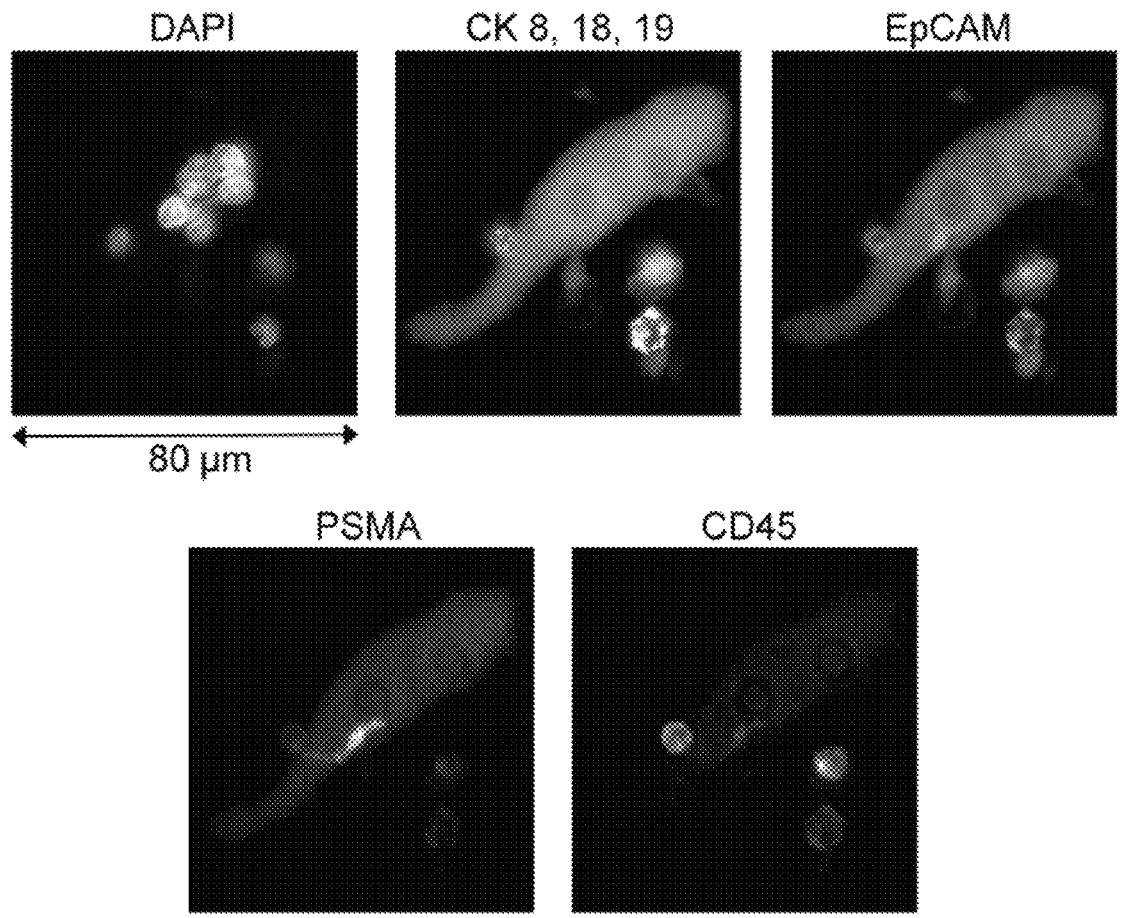
FIG. 22 is an example of a CAML from a prostate cancer patient also stained for PSMA.

We propose that CAML represents a specialized TAM initiating at the site of tumor and disseminating into circulation. This would be consistent with previous publications characterizing TAMs at the primary tumor site, as well as the observations that CAMLs appear CD14+, have engulfed epithelial tissue, and occur exclusively in cancer patients. To understand the origin of CAMLs, we looked at whether they arise from circulating monocytes or directly from DTAMs. As TAMs and monocytes would both present with similar protein markers, we assessed the presence of engulfed organ-specific markers, Pancreatic Duodenal Homeobox-1 (PDX-1) for pancreatic patients or Prostate-Specific Membrane Antigen (PSMA) for prostate patients. PDX-1 is a differentiation and development marker found in adult endocrine organs, namely pancreatic cells. PSMA is a membrane glycoprotein, which is highly expressed in prostate cells. After isolating and enumerating CAMLs, we re-stained pre-identified CAML samples with PSMA or PDX-1. A PDX-1 positive reaction was seen in all CAMLs from pancreatic samples (FIG. 21), while PSMA was found in all CAMLs from prostate samples (FIG. 22). While possible that cellular fusion or ingestion of debris occurred away from the tumor site, the high concentration of markers coupled with the scarcity of tumor debris in circulation make this unlikely. Instead, we interpret this suite of biomarker staining as evidence that CAMLs are a subtype of DTAMs, and that staining occurred from phagocytosed necrotic debris, or engulfed neoplastic cells from the tumor site.

TABLE 2

Cell markers used to analyze the CAMLs.

| Cell Type | PDX-1 | PSMA | CD11c | CD14 | CD146 | TIE-2 (C202b) | Cytokeratin 8, 18 & 19 | EpCAM (CD326) | CD45 (LCA) |
|---|---|---|---|---|---|---|---|---|---|
| CCAMLC | +(*) | +(‡) | + | +/− | +/− | +/− | + | + | +/− |
| Breast CTC | − | − | − | − | − | − | + | +/− | − |
| Prostate CTC | − | + | − | − | − | − | + | +/− | − |
| Pancreas CTC | + | − | − | − | − | − | + | +/− | − |
| Epithelial Cell | − | − | − | − | − | − | + | + | − |
| Monocyte | − | − | + | + | −(♦) | −(♦) | − | − | + |
| Endothelial Cell | − | − | − | − | + | + | + | − | − |
| White Blood Cell | − | − | −(o) | −(o) | − | − | − | − | + |

(+) Positive in the majority of cell types; (−) negative in the majority of cell types; (+/−) cell populations heterogenous for this marker and may be positive or negative; (*)found only in cells from pancreatic cancer patients; (‡)found only in cells from prostate cancer patients; (♦)a small subset population on monocytes are positive for this marker; (o)monocytes are a subpopulation of white blood cells and will express these markers.

Figure 23:
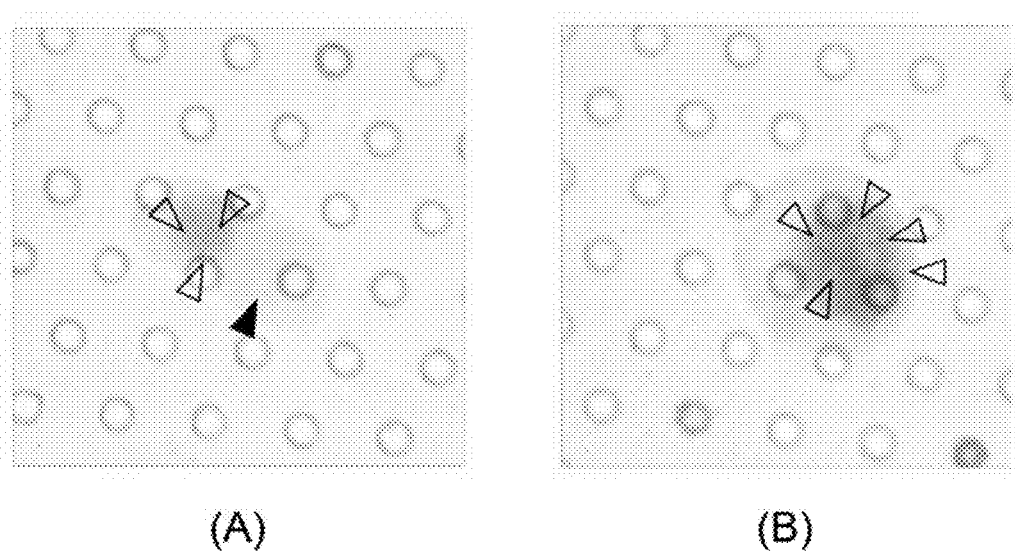
FIGS. 23A-B show H&E staining of CAMLs. Two representative CAMLs cells (A) and (B) are shown under a light microscope. The blocked arrow is a round vacuole located within the cytoplasm of the CAML. Open arrows show the individual nuclei and subsequent polynuclear nature of the CAMLs.

FIG. 23 shows H & E Staining of CAMLs. Samples from breast cancer patients were identified by fluorescent DAPI and cytokeratin stains. Filters were then re-stained by Hematoxylin and by Eosin Y. Two representative CAMLs cells are shown under a light microscope. The blocked arrow is a round vacuole located within the cytoplasm of the CAML. Open arrows show the individual nuclei and subsequest polynuclear nature of the CAMLs (A) An oval shaped CAMLs that has 3 visible nuclei and a vacuole (B) Round shaped CAML that has 5 visible nuclei.

Figure 24A:
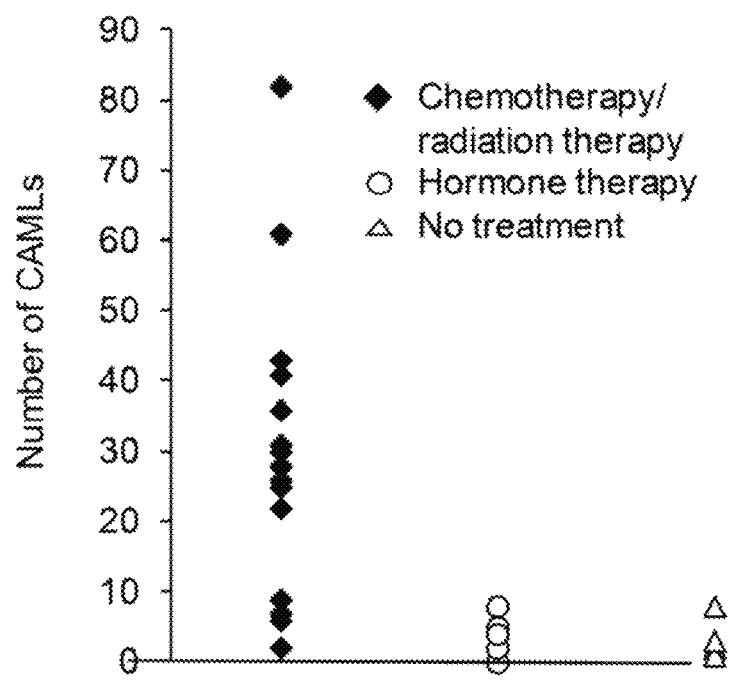
FIG. 24A is a plot of the number of circulating cancer associated macrophage-like cells (CAMLs) in breast cancer patients with no treatment, and hormone treatment or chemotherapy and radiation therapy.
Figure 24B:
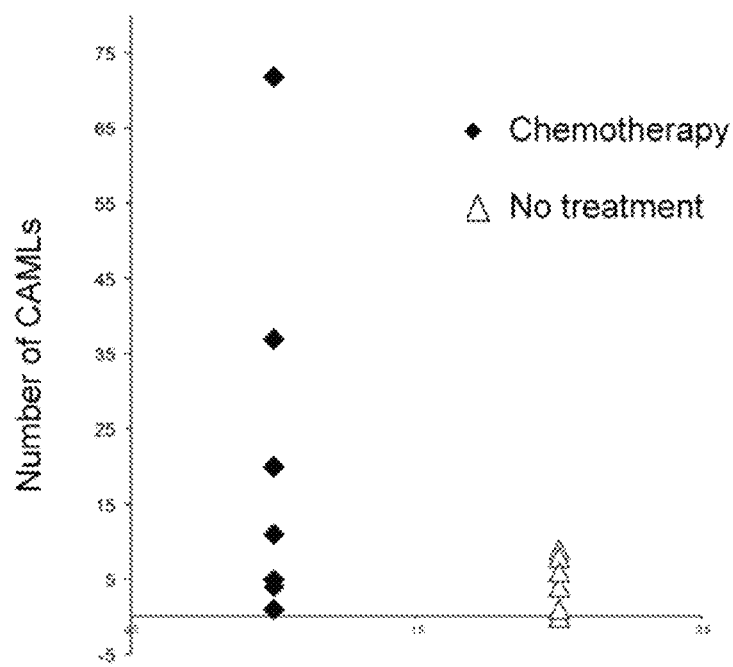
FIG. 24B is a plot of the number of circulating cancer associated macrophage-like cells (CAMLs) in pancreatic cancer patients with no treatment, and chemotherapy and radiation therapy.

To further test whether CAMLs are a DTAM subtype, we compared therapy regimes and temporal changes in the number of CAMLs in relation to cancer progression and stability. We hypothesized that if CAMLs are associated with phagocytosis of cellular debris due to cytotoxicty at the tumor site, i.e. derived from TAMs, then patients not chemoresponsive or undergoing only hormone therapy would not produce additional cellular debris and thus would have no change in CAML numbers. Conversely, patients that are responsive to chemotherapy would have an increase in CAMLs. Analysis of therapeutic regimes showed that only chemotherapy, not hormonal nor non-therapy was associated with an increase in CAML levels in breast cancer patients (FIG. 24A) and pancreatic cancer patients (FIG. 24B). For Pancreatic cancer patients, CAMLs for chemotherapy average is 16.4 CAMLs, and for no therapy is 4.1. We find that non-treated and hormone treated patients, who should show little change in tumor size, have low numbers of CAMLs <0.4-0.6/mL blood (FIGS. 24A-B). Conversely, if a chemotherapeutic regime was in use, CAML numbers increased to 3.9/mL. These data suggest that CAMLs may provide a sensitive representation of phagocytosis at the tumor site that could quantify a cell-specific immune response to the extent of cellular debris caused by chemotherapy.

Figure 25:
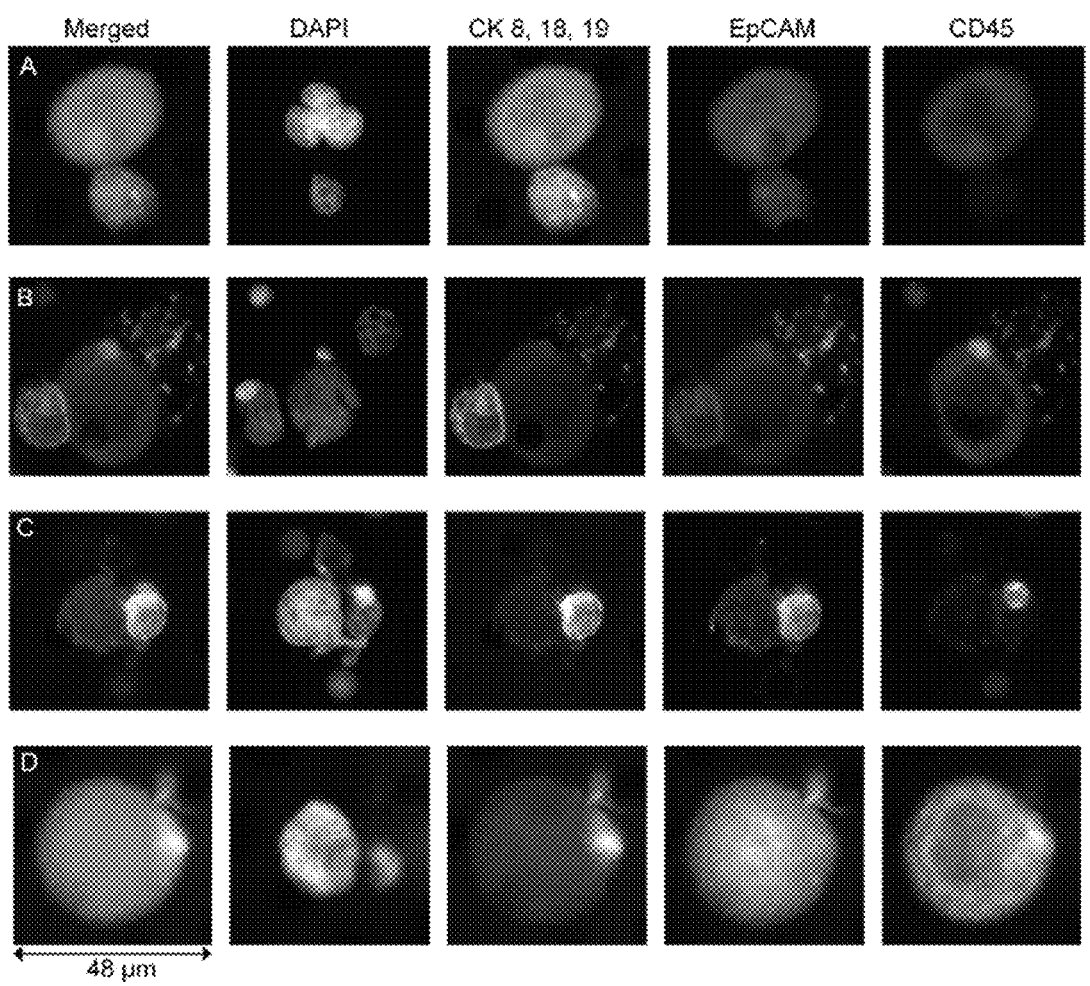
FIG. 25A shows a CTC associated with a CAML.
FIG. 25B shows a CTC bound to a CAML.
FIG. 25C shows a CTC bound to a CAML with membrane fusing.
FIG. 25D shows a CAML that engulfed a CK positive cell.
Figure 26:
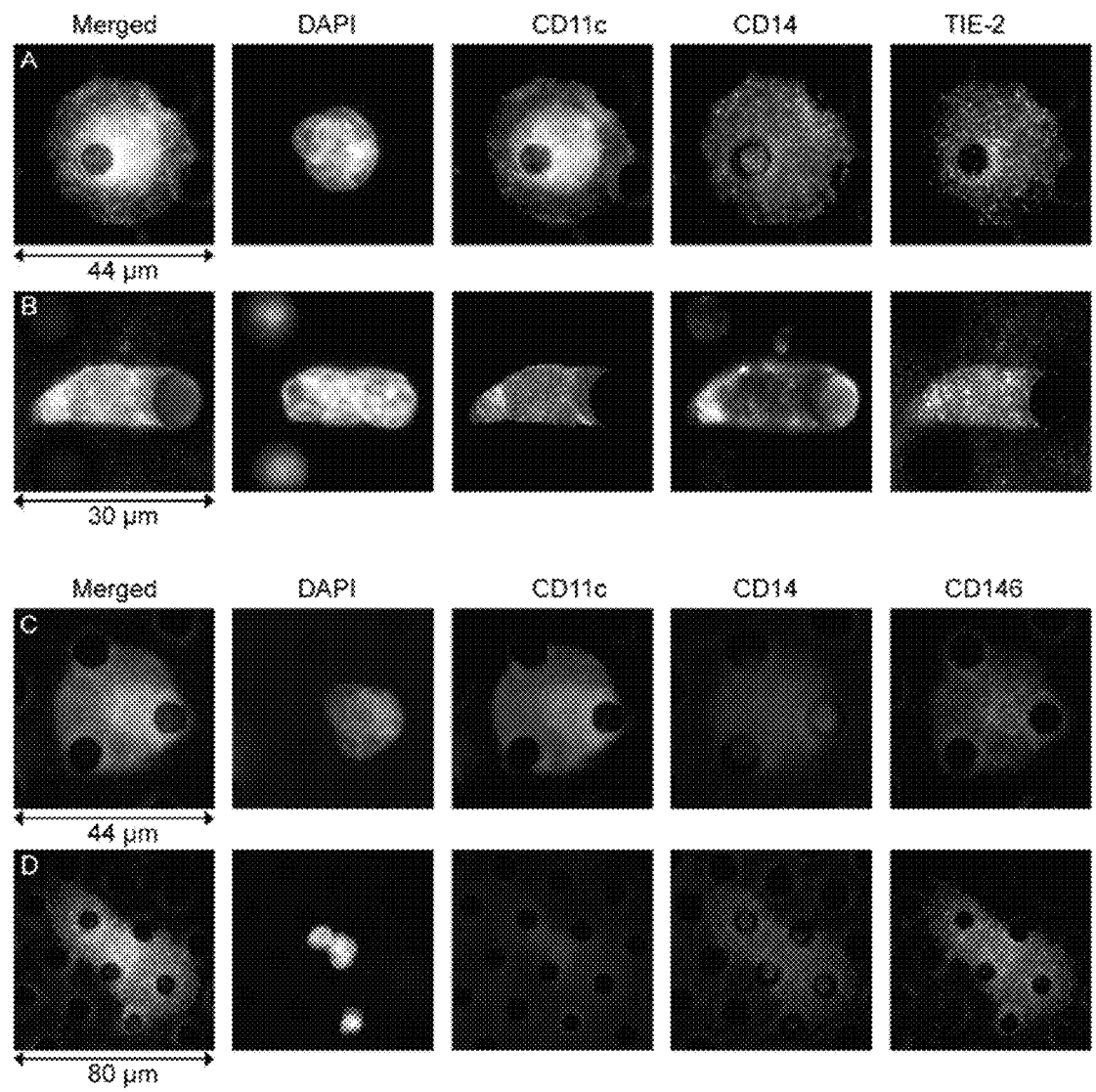
FIG. 26A shows examples of CAML from breast cancer patient stained for CD11c, CD14 and TIE-2.
FIG. 26B shows examples of CAML from pancreatic cancer patient stained for CD11c, CD14 and TIE-2.
FIG. 26C shows examples of CAML from breast cancer patient stained for CD11c, CD14 and CD146.
FIG. 26D shows examples of CAML from pancreatic cancer patient stained for CD11c, CD14 and CD146.

CTCs originate at a tumor site, circulate in peripheral blood, and have the ability to seed metastatic sites. However, the pathway for CTC detachment and invasion into the circulatory system is a complex process. We analyzed CAMLs isolated from patient samples for evidence of a CTC/CAML interaction. CTCs were found bound to CAMLs in 3 of 72 patients, all in metastatic disease (FIGS. 25A-25C). In addition, three instances of CAMLs were found with engulfed cells that appeared to have a neoplastic/CTC phenotype (FIG. 25D). Representing 7% of patients, the observed interaction of a dual pair CTC and CAML is indicative of two possibilities. First, these cells attached while in circulation, implying that CAMLs are an active immune response to cancer cells in blood. Second, these cells bind at the primary tumor and disseminated together into circulation, implying a similar pathway of intravasation. In either case, this pairing of cells suggests that CAMLs may play a role in the immune response to cancer cell migration in the peripheral blood of cancer patients.

Circulating monocytes have the ability to enter any tissue compartment of the body, including lymph nodes, bone marrow, most organs, and even cross the blood brain barrier. Angiogenic Endothelial Progenitor Cells (EPCs) with neovascular potential are capable of being derived from macrophages, and TIE-2+ (CD202b) macrophages are intricately involved in tumor vascularization. Recent in vitro and mouse in vivo experiments have shown that EPCs derived from CD14+/CD11c+ monocytes differentiate into CD146+/TIE-2+ endothelial cells capable of pro-angiogenic activity. As CAMLs presented with an EPC-like spindle phenotype, we analyzed CAMLs for evidence of this pathway. After identifying CAML positive samples, we stained CAMLs with panels of monocytic markers, CD11c and CD14, as well as angiogenic endothelial markers, CD146 or TIE-2 (FIGS. 26A-26D). We observed CAMLs positive for both monocytic and endothelial markers. The monocytic marker CD11c was the most reactive, found in all CAMLs stained, while a secondary monocytic marker CD14 was the least reactive, at times negative. The pro-angiogenic marker (TIE-2) and endothelial marker (CD 146) stained positive in CAMLs, but staining intensity was intermittent. The endothelial/monocytic overlap findings are not surprising, as circulating monocytes have high morphological and marker heterogeneity. Even today there is great debate over the mononuclear phagocytic system for classification as endothelial cells, bone marrow-derived cells and monocytic cell express overlapping markers and have similar developmental pathways. Nevertheless, the presence of CD146, or TIE-2, on CD14 positive cells indicates a specialized pro-angiogenic macrophage capable of neovascular potential.

Although many studies have focused on dissemination of CTCs, TAMs may be involved in seeding, proliferation and neovascularization of metastases. While previous studies provide evidence for vascular infiltration of tumor cells through macrophage assistance, our results now also supply evidence of macrophage interaction with tumor cells in the circulation. We hypothesis that CAMLs originating at the primary tumor disseminate into the circulation. We also show that CAMLs bind to and migrate through the circulation attached to CTCs, possibly disseminating in conjunction. Finally, we describe pro-angiogenic TIE-2/CD146-expressing CAMLs, indicating the ability to neovascularize a metastatic microenvironment. These data provide clinical evidence that pro-angiogenic cells migrate bound to CTCs, suggesting a link between intravasation, migration and extravasation of CTCs.

Capture of CAMLS and CTCs

Cells larger and/or less flexible than other cells present in a bodily fluid may be collected by filtering the bodily fluid. For example, targeted cells indicative of a condition may be collected by passing a bodily fluid through a filter having openings that are too small for the target cells to pass through, but large enough for other cells to pass through. Once collected, any number of analyses of the target cells may be performed. Such analyses may include, for example, identifying, counting, characterizing expressions of markers, obtaining molecular analysis, and/or culturing the collected cells.

CAMLs, pathologically-definable CTCs, and apoptotic CTCs are larger than red blood cells and most white blood cells. Using a precision microfilter that has precision pore size and pore distribution has been shown to provide high capture efficiency and low standard of deviation. CellSieve™ microfilters (Creatv MicroTech) are one example of precision microfilters. CellSieve™ microfilters are transparent and nonfluorescent making them ideal for microscope imaging analysis. Pore sizes of 7-8 microns eliminated all the red blood cells and 99.99% of the white blood cells. Methods to fabricate microfilters producing uniform pore size and distribution are described in WO 2011/139445, and PCT/US12/66390, both of which is incorporated herein by reference in their entireties. Microfilters made by a track etch method have randomly located pores that can overlap resulting in effectively large pores. They might lose some CAMLs and CTCs.

Many other methods exist for captures of CTCs. Some can also be adopted to capture CAMLs. They generally break-down into the following categories:

Since CAMLs are large compared with majority of blood cells, any size based method is suitable for capturing CAMLs. Microfilters are ideal for capture of CAMLs and CTCs. Microfluidic chips technologies that sort, select, group, trapping, concentrates large cells or eliminate small cells by size are also suitable.

Immunocapture use ferrofluids, magnetic beads, microfluidic chips, etc, coated with antibody for selection of CAMLs, or elimination of other cells.

Red blood cell lysis can also be used for collecting CAMLs. The resultant sample volume requires plating on multiple glass slides.

FICOLL.

Flow cytometry.

A variety of microfluidic chip utilizing a variety of biological and physical principles.

Summary of Clinical Utilities

These results support the idea that CAMLs provide a robust indicator of cancer presence.

The sensitivity and specificity of the utility of CAMLs can be further improved in combination with simultaneous detection of CTCs.

Cancer screening is a strategy used in a population to identify an unrecognised disease in individuals without signs or symptoms, with pre-symptomatic or unrecognised symptomatic disease. As such, screening tests are somewhat unique in that they are performed on persons apparently in good health. A screening test is not a diagnostic test. Diagnostic testing is a procedure performed to confirm, or determine the presence of disease in an individual suspected of having the disease.

CAMLs can be used as a cancer diagnostic to provide additional non-invasive diagnostics to confirm other screening techniques, such as mammography, PSA and CAl25.

Since CAMLs can be found in stage I and II of cancer, CAMLs can be used as screening for early detection of carcinomas of epithelial origin especially for high risk patients for lung, pancreatic, colorectal and other cancers that does not have early detection methods. Specificity of the type of cancer can be determined by staining for various cancer site specific markers. Some examples are (i) use antibody against PSMA to specifically identifying prostate cancer, (ii) use antibody against PDX-1 to specifically identifying lung cancer, (iii) antibody against CAl25 for ovarian cancer, and (iv) clorotoxin to identify glioma.

Similarly CAMLs can be used to determine early recurrence of cancer when the cancer was under remission. Currently CT and MRI are used to monitor the patient's tumor, requiring the tumor to change in size substantially to notice the difference. Patients can therefore lose valuable time in beginning treatment when only subtle size changes occur. CAMLs, alone or in combination with CTCs, can provide early detection of return of cancer. Non-invasive blood test of CAMLs and CTCs is much lower in cost than CT and MRI.

The capability of tracking CAMLs provides a novel opportunity to routinely monitor necrosis and chemotherapy or radiation therapy response. If the chemotherapy is not working, the CAMLs number will not increase. This can be used in parallel with CTC detection. If the treatment is working, the number of pathologically-definable CTCs will decrease and number of apoptotic CTCs will increase. However, CTCs cannot always be detected. If CTCs are detected at the same time as CAMLs, the sensitivity and specificity can be improved. For many cancers there are large array of chemotherapy agents. If the patient is not responding to one type of chemotherapy, the patient can quickly switch to another.

The CAMLs can also potentially be used to determine cancer subtyping or gene mutations, translocations or amplification. There are a number of cancerous nuclei in each CAMLs. Thus, molecular analysis of the nucleus for genetic mutation, genetic defects, gene translocations can provide information to determine treatments. There are drugs that specifically target certain gene mutations, translocation or amplifications. CAMLs can be used along or in parallel with CTCs for molecular analysis.

Circulating monocytes have the ability to enter any tissue compartment of the body, including lymph nodes, bone marrow, most organs, and even cross the blood brain barrier. The detection of CAMLs are not limited to blood, but also can be found in lymph nodes, bone marrow, cerebral spinal fluid, most organs, and urine.

The volume of blood typically used for detection of CTCs is 7.5 mL. Larger volumes of blood will provide more sensitivity and consistency, but smaller volumes such as 3.5 mL may be sufficient. For many CTC detection methods, larger volumes of blood are not practical for a variety of reasons. However, microfiltration of blood to capture CTCs and/or CAMLs allows more flexibility to increase the sample size. Blood volumes of 50 mL have been shown to be successfully screened using CellSieve™ microfilters with 160,000 pores. The recommended volume of blood to capture CAMLs would be 7.5 ml or greater.

We claim:

1. A method of screening a subject for cancer, comprising detecting circulating Cancer Associated Macrophage-Like cells (CAMLs) in a biological sample from a subject previously determined to be high risk for cancer, wherein said detecting comprises:
    (a) isolating intact cells of between 20 and 300 micron in size from a biological sample obtained from a subject using a microfilter having pores of about 7-8 micros, wherein the biological sample is peripheral blood, and
    (b) selecting multi-nucleated cells isolated in (a) expressing one or more of the following markers: endothelial cell markers CD146, CD202b, and CD31, and monocyte cell markers CD11c and CD14, wherein antibodies are used to select cells expressing the one or more markers, thereby detecting CAMLs in a biological sample from a subject,
    wherein when CAMLs are detected in the biological sample, the subject is determined to have cancer.

2. The method of claim 1, wherein the cancer is carcinoma or solid tumor.

3. The method of claim 1, further comprising detecting circulating tumor cells (CTCs) in the biological sample.

4. A method for confirming a diagnosing of cancer in a subject, comprising detecting CAMLs in a biological sample from a subject previously diagnosed with cancer, wherein said detecting comprises:
    (a) isolating intact cells of between 20 and 300 micron in size from a biological sample obtained from a subject using a microfilter having pores of about 7-8 microns, wherein the biological sample is one or more of peripheral blood, blood, and lymph nodes, and
    (b) selecting multi-nucleated cells isolated in (a) expressing one or more of the following markers: endothelial cell markers CD146, CD202b, and CD31, and monocyte cell markers CD11c and CD14, wherein antibodies are used to select cells expressing the one or more markers, thereby detecting CAMLs in a biological sample from a subject,
    wherein when CAMLs are detected in the biological sample, the diagnosed of cancer in the subject is confirmed.

5. The method of claim 4, further comprising detecting CTCs in the biological sample, wherein when CAMLs and CTCs are detected in the biological sample, the subject is diagnosed with cancer.

6. The method of claim 1 or 4, wherein intact cells of between 20 and 300 micron in size are isolated using a low-pressure microfiltration assay.

7. The method of claim 1 or 4, wherein the cancer is breast, prostate, lung, pancreatic, or colorectal.

8. A method for monitoring efficacy of a cancer treatment, comprising (a) determining the number of CAMLs in a biological sample from a subject previously diagnosed with cancer before treatment of the subject for cancer, and (b) comparing the number of CAMLs determined in (a) to a number of CAMLs determined from a similar biological sample from the same subject at one or more time points after treatment, wherein the number of CAMLs in a biological sample is determining by:

(a) isolating intact cells of between 20 and 300 micron in size from a biological sample obtained from a subject using a microfilter having pores of about 7-8 microns, wherein the biological sample is one or more of peripheral blood, blood, and lymph nodes, and (b) selecting multi-nucleated cells isolated in (a) expressing one or more of the following markers: endothelial cell markers CD146, CD202b, and CD31, and monocyte cell markers CD11c and CD14, wherein antibodies are used to select cells expressing the one ore more markers, to obtain CAMLs from the biological sample.

9. The method of claim 8, further comprising (c) determining the number of CTCs in the biological sample of (a), and (d) comparing the number of CTCs determined in (c) to a number of CTCs determined from the biological sample of (b).

10. The method of claim 8, wherein intact cells of between 20 and 300 micron in size are isolated using a low-pressure microfiltration assay.

11. The method of claim 8, wherein the cancer is breast, prostate, lung, pancreatic, or colorectal.

12. A method for detecting CAMLs in a biological sample from a subject, comprising:

(a) isolating intact cells of between 20 and 300 micron in size from a biological sample obtained from a subject, wherein the biological sample is peripheral blood, and (b) detecting multi-nucleated cells isolated in (a) that express one or more of the following markers: endothelial cell markers CD146, CD202b, and CD31, and monocyte cell markers CD11c and CD14, wherein antibodies are used to detect cells that express the one or more markers, thereby detecting CAMLs is a biological sample from a subject.

13. The method of claim 12, wherein the subject has cancer.

14. The method of claim 13, wherein the cancer is carcinoma or solid tumor.

15. The method of claim 12, further comprising detecting CTCs in the biological sample.

16. The method of claim 12, wherein intact cells of between 20 and 300 micron in size are isolated using one or more means selected from the group consisting of size exclusion methodology, red blood cell lysis, FICOLL, a microfluidic chip, and flow cytometry, or a combination thereof.

17. The method of claim 16, wherein the size exclusion methodology comprises use of a microfilter.

* * * * *